(12) United States Patent
Tam et al.

(10) Patent No.: US 9,023,452 B2
(45) Date of Patent: *May 5, 2015

(54) RIGID STRUCTURAL AND LOW BACK FACE SIGNATURE BALLISTIC UD/ARTICLES AND METHOD OF MAKING

(75) Inventors: Thomas Yiu-Tai Tam, Chesterfield, VA (US); John Armstrong Young, Midlothian, VA (US); Ronnie Moore, Midlothian, VA (US); David A Hurst, Richmond, VA (US)

(73) Assignee: Honeywell International Inc., Morristown, NJ (US)

( * ) Notice: Subject to any disclaimer, the term of this patent is extended or adjusted under 35 U.S.C. 154(b) by 298 days.

This patent is subject to a terminal disclaimer.

(21) Appl. No.: 13/594,763

(22) Filed: Aug. 24, 2012

(65) Prior Publication Data

US 2014/0302274 A1 Oct. 9, 2014

Related U.S. Application Data

(60) Provisional application No. 61/531,323, filed on Sep. 6, 2011.

(51) Int. Cl.
*F41H 1/02* (2006.01)
*G01N 19/00* (2006.01)
*D06M 17/00* (2006.01)
*G01N 3/40* (2006.01)
*F41H 5/04* (2006.01)
*G01N 3/32* (2006.01)
*B32B 37/24* (2006.01)

(52) U.S. Cl.
CPC ......... *G01N 19/00* (2013.01); *Y10T 428/24124* (2013.01); *D06M 17/00* (2013.01); *F41H 1/02* (2013.01); *G01N 3/40* (2013.01); *F41H 5/0485* (2013.01); *G01N 3/32* (2013.01); *G01N 2203/0096* (2013.01); *B32B 37/24* (2013.01)

(58) Field of Classification Search
CPC ............ G01N 3/32; G01N 19/00; F41H 1/02; F41H 5/0485; B32B 37/24
USPC .................. 428/113, 105, 107, 156, 213, 364
See application file for complete search history.

(56) References Cited

U.S. PATENT DOCUMENTS

| | | | |
|---|---|---|---|
| 4,091,855 A | 5/1978 | Sibilia et al. | |
| 4,161,874 A | 7/1979 | Specker et al. | |
| 4,691,556 A | 9/1987 | Mellander et al. | |
| 4,952,361 A | 8/1990 | Cree | |
| 5,001,008 A | 3/1991 | Tokita et al. | |
| 5,075,904 A | 12/1991 | Shirasaki et al. | |
| 5,139,079 A | 8/1992 | Becraft et al. | |
| 5,139,873 A | 8/1992 | Rebouillat | |
| 5,178,802 A | 1/1993 | Cree et al. | |
| 5,534,343 A | 7/1996 | Landi et al. | |
| 5,545,455 A | 8/1996 | Prevorsek et al. | |
| 5,569,528 A | 10/1996 | Van der Loo et al. | |
| 5,573,850 A | 11/1996 | Cunningham et al. | |
| 5,591,933 A | 1/1997 | Li et al. | |
| 5,601,775 A | 2/1997 | Cunningham et al. | |
| 5,677,029 A | 10/1997 | Prevorsek et al. | |
| 5,710,426 A | 1/1998 | Reed et al. | |
| 6,058,784 A | 5/2000 | Carroll et al. | |
| 6,098,465 A | 8/2000 | Matsumoto et al. | |
| 6,146,013 A | 11/2000 | Huetter et al. | |
| 6,326,427 B1 | 12/2001 | Birnbrich et al. | |
| 6,389,906 B2 | 5/2002 | Buck | |
| 6,607,859 B1 | 8/2003 | Tanaka et al. | |
| 6,630,231 B2 | 10/2003 | Perez et al. | |
| 6,691,585 B2 | 2/2004 | Ahn | |
| 6,880,385 B2 | 4/2005 | Esser et al. | |
| 7,073,538 B2 | 7/2006 | Bhatnagar et al. | |
| 7,204,165 B1 | 4/2007 | Plaga et al. | |
| 7,718,245 B2 | 5/2010 | Bhatnagar et al. | |
| 7,919,418 B2 | 4/2011 | Bhatnagar et al. | |
| 7,964,518 B1 | 6/2011 | Bhatnagar et al. | |
| 8,080,486 B1 | 12/2011 | Bhatnagar et al. | |
| 2001/0031594 A1 | 10/2001 | Perez et al. | |
| 2003/0033655 A1 | 2/2003 | Kavesh | |
| 2003/0199215 A1 | 10/2003 | Bhatnagar et al. | |
| 2004/0023580 A1 | 2/2004 | Hand et al. | |
| 2004/0221712 A1* | 11/2004 | Stewart et al. ............... 89/36.05 |
| 2007/0016251 A1 | 1/2007 | Roby | |
| 2007/0117483 A1 | 5/2007 | Bhatnagar et al. | |
| 2008/0139071 A1 | 6/2008 | Bhatnagar et al. | |
| 2008/0289438 A1 | 11/2008 | Bertocci | |
| 2009/0093180 A1 | 4/2009 | Park et al. | |
| 2009/0115099 A1 | 5/2009 | Goossens et al. | |

(Continued)

FOREIGN PATENT DOCUMENTS

| | | |
|---|---|---|
| CN | 101603797 | 12/2009 |
| JP | 1986-241330 | 10/1986 |
| JP | 61241330 | 10/1986 |
| JP | 62169827 | 7/1987 |
| JP | 62184111 | 8/1987 |
| JP | 2269828 | 11/1990 |
| JP | 05-044154 | 2/1993 |
| JP | 05209370 | 8/1993 |
| JP | 06212504 | 8/1994 |
| JP | 6-346372 | 12/1994 |

(Continued)

OTHER PUBLICATIONS

Yang, Zingzhou (James), and Jichang Dai, "Simulation-Based Assessment of Rear Effect to Ballistic Helmet Impact." Computer-Aided Design & Applications, 7(1), 2010, pp. 59-73.

(Continued)

*Primary Examiner* — Brent O'Hern

(57) ABSTRACT

Fabrication of ballistic resistant fibrous composites having improved ballistic resistance properties. More particularly, ballistic resistant fibrous composites having enhanced a dynamic storage modulus, which correlates to low composite backface signature.

11 Claims, No Drawings

(56) References Cited

U.S. PATENT DOCUMENTS

| | | | |
|---|---|---|---|
| 2009/0197969 | A1 | 8/2009 | Poulsen et al. |
| 2009/0211894 | A1 | 8/2009 | Ribeiro De Almeida Carneiro Pacheco et al. |
| 2009/0282596 | A1 | 11/2009 | Carbajal et al. |
| 2009/0305038 | A1 | 12/2009 | Duran et al. |
| 2010/0048076 | A1 | 2/2010 | Creyghton et al. |
| 2010/0056006 | A1 | 3/2010 | Campbell |
| 2010/0173156 | A1 | 7/2010 | Morin |
| 2010/0196671 | A1 | 8/2010 | Sorensen et al. |
| 2010/0307223 | A1 | 12/2010 | Jeftic-Stojanovski et al. |
| 2011/0041679 | A1 | 2/2011 | Pollock et al. |
| 2011/0123757 | A1 | 5/2011 | Howland |
| 2011/0189419 | A1 | 8/2011 | Le et al. |
| 2012/0022221 | A1 | 1/2012 | Hidalgo et al. |
| 2013/0055790 | A1 | 3/2013 | Bhatnagar et al. |
| 2013/0059112 | A1 | 3/2013 | Tam et al. |
| 2013/0059494 | A1 | 3/2013 | Tam et al. |
| 2013/0059496 | A1 | 3/2013 | Ardiff et al. |
| 2013/0115839 | A1 | 5/2013 | Arvidson et al. |
| 2014/0248463 | A1* | 9/2014 | Tam et al. ............ 428/113 |
| 2014/0302273 | A1* | 10/2014 | Tam et al. ............ 428/113 |

FOREIGN PATENT DOCUMENTS

| | | |
|---|---|---|
| JP | 7-138877 | 5/1995 |
| JP | 07135087 | 5/1995 |
| JP | 08049998 | 2/1996 |
| JP | 2001-262469 | 9/2001 |
| JP | 2005-179840 | 7/2005 |
| JP | 2007-191801 | 8/2007 |
| JP | 2007-538172 | 12/2007 |
| KR | 10-2001-0047275 | 6/2001 |
| KR | 10-0567442 | 4/2006 |
| KR | 10-0601829 | 7/2006 |
| SE | 200400725 | 9/2005 |
| WO | 93-00564 | 1/1993 |
| WO | 2006040754 | 4/2006 |
| WO | 2007057595 | 5/2007 |
| WO | 2007148365 | 12/2007 |
| WO | 2008137218 | 11/2008 |
| WO | 2010112743 | 10/2010 |
| WO | 2010123593 | 10/2010 |
| WO | 2011015620 | 2/2011 |

OTHER PUBLICATIONS

Aare, Magnus, and Svein Kleiven, "Evaluation of Head Response to Ballistic Helmet Impacts Using the Finite Element Method." International Journal of Impact Engineering 34 (2007), pp. 596-608.

"Body Armor Follow-Up Testing Component Launched." TechBeat, Fall 2010, National Law Enforcement and Corrections Technology Center, National Institute of Justice.

"Supplement 1: Status Report to the Attorney General on Body Armor Safety Initiative Testing and Activities." National Institute of Justice, Dec. 27, 2004.

"Bullet Resistant Helmet" Test Procedure, H.P. White Laboratory, Inc., Oct. 1995.

"NIJ Standard for Ballistic Helmets." Technology Assessment Program, Dec. 1981.

"Ballistic Resistance of Personal Body Armor, NIJ Standard-0101.04," National Institute of Justice, Law Enforcement and Corrections Standards and Testing Program, Sep. 2000.

"Head Strong: ARL Team Determined to Find New Solutions for Improved Soldier Helmet Systems," Mar. 1, 2011.

"Test and Evaluation Report on Marine Corps Combat Helmets," Apr. 8, 2001.

Reed, Katherine E., "Dynamic Mechanical Analysis of Fiber Reinforced Composites" NASA Technical Memorandum 79033, Lewis Research Center Cleveland, Ohio, 1979.

Pappas, Daphne. "Status and potential of atmospheric plasma processing of materials." U.S. Army Research Laboratory, APG Maryland; Mar. 2, 2011; pp. 021301-1 to 021301-17.

Moon, S.I. et al., "The Effect of the Oxygen-Plasma Treatment of UHMWPE Fiber on the Transverse Properties of UHMWPE-Fiber/Vinylester Composites." Composites Science and Technology, vol. 59 (Mar. 1999), pp. 487-493, Seoul, South Korea.

Unpublished U.S. Appl. No. 13/594,735, filed Aug. 24, 2012.

Unpublished U.S. Appl. No. 13/594,747, filed Aug. 24, 2012.

Guo et al., "Effects of Air Plasma Treatment on Tribological Properties of Hybrid PTFE/Kevlar Fabric Composite." Journal of Applied Polymer Science, vol. 114, p. 3980-3986 (2009).

Ashok Bhatnagar, "Lightweight Ballistic Composites, Military and Law-Enforcement Applications," Woodhead Publishing Limited, Cambridge, England, pp. 282-283 (2006).

* cited by examiner

RIGID STRUCTURAL AND LOW BACK FACE SIGNATURE BALLISTIC UD/ARTICLES AND METHOD OF MAKING

CROSS-REFERENCE TO RELATED APPLICATION

This application claims the benefit of co-pending U.S. Provisional Application Ser. No. 61/531,323, filed on Sep. 6, 2011, the disclosure of which is incorporated by reference herein in its entirety.

BACKGROUND OF THE INVENTION

1. Field of the Invention

The invention pertains to ballistic resistant fibrous composites having an enhanced dynamic storage modulus while maintaining superior ballistic resistance properties. The enhanced dynamic storage modulus correlates to low composite backface signature.

2. Description of the Related Art

Ballistic resistant articles fabricated from composites comprising high strength synthetic fibers are well known. Articles such as bullet resistant vests, helmets, vehicle panels and structural members of military equipment are typically made from fabrics comprising high strength fibers such as SPECTRA® polyethylene fibers or Kevlar® aramid fibers. For many applications, such as vests or parts of vests, the fibers may be used in a woven or knitted fabric. For other applications, the fibers may be encapsulated or embedded in a polymeric matrix material and formed into non-woven fabrics. For example, U.S. Pat. Nos. 4,403,012, 4,457,985, 4,613,535, 4,623,574, 4,650,710, 4,737,402, 4,748,064, 5,552,208, 5,587,230, 6,642,159, 6,841,492, 6,846,758, all of which are incorporated herein by reference, describe ballistic resistant composites which include high strength fibers made from materials such as extended chain ultra-high molecular weight polyethylene ("UHMW PE"). Ballistic resistant composites fabricated from such high strength synthetic fibers exhibit varying degrees of resistance to penetration by high speed impact from projectiles such as bullets, shells, shrapnel and the like, as well as varying degrees of backface signature resulting from the same projectile impact.

It is known that each type of high strength fiber has its own unique characteristics and properties. In this regard, one defining characteristic of a fiber is the ability of the fiber to bond with or adhere with surface coatings, such as resin coatings. For example, ultra-high molecular weight polyethylene fibers are relatively inert, while aramid fibers have a high-energy surface containing polar functional groups. Accordingly, resins generally exhibit a stronger affinity aramid fibers compared to the inert UHMW PE fibers. Nevertheless, it is also generally known that synthetic fibers are naturally prone to static build-up and thus typically require the application of a fiber surface finish in order to facilitate further processing into useful composites. Fiber finishes are employed to reduce static build-up, and in the case of untwisted and unentangled fibers, to aid in maintaining fiber cohesiveness. Finishes also lubricate the surface of the fiber, protecting the fiber from the equipment and protecting the equipment from the fiber. The art teaches many types of fiber surface finishes for use in various industries. See, for example, U.S. Pat. Nos. 5,275,625, 5,443,896, 5,478,648, 5,520,705, 5,674,615, 6,365,065, 6,426,142, 6,712,988, 6,770,231, 6,908,579 and 7,021,349, which teach spin finish compositions for spun fibers.

However, typical fiber surface finishes are not universally desirable. One notable reason is because a fiber surface finish can interfere with the interfacial adhesion or bonding of polymeric binder materials on fiber surfaces, including aramid fiber surfaces. Strong adhesion of polymeric binder materials is important in the manufacture of ballistic resistant fabrics, especially non-woven composites such as non-woven SPECTRA SHIELD® composites produced by Honeywell International Inc. of Morristown, N.J. Insufficient adhesion of polymeric binder materials on the fiber surfaces may reduce fiber-fiber bond strength and fiber-binder bond strength and thereby cause united fibers to disengage from each other and/or cause the binder to delaminate from the fiber surfaces. A similar adherence problem is also recognized when attempting to apply protective polymeric compositions onto woven fabrics. This detrimentally affects the ballistic resistance properties (anti-ballistic performance) of such composites and can result in catastrophic product failure.

The anti-ballistic performance of composite armor can be characterized in different ways. One common characterization is the $V_{50}$ velocity. For composites of equal areal density (i.e. the weight of the composite panel divided by the surface area) the higher the $V_{50}$ the better the penetration resistance of the composite. However, even when anti-ballistic armor is sufficient to prevent the penetration of a projectile, the impact of the projectile on the armor may also cause significant non-penetrating, blunt trauma ("trauma") injuries. Accordingly, another important measure of anti-ballistic performance is armor backface signature. Backface signature ("BFS"), also known in the art as backface deformation or trauma signature, is the measure of the depth of deflection of body armor due to a bullet impact. When a bullet is stopped by composite armor, potentially resulting blunt trauma injuries may be as deadly to an individual as if the bullet had penetrated the armor and entered the body. This is especially consequential in the context of helmet armor, where the transient protrusion caused by a stopped bullet can still cross the plane of the wearer's skull and cause debilitating or fatal brain damage.

It is known that the $V_{50}$ ballistic performance of a composite is directly related to the strength of the constituent fibers of the composite. Increases in fiber strength properties such as tenacity and/or tensile modulus are known to correlate with an increase in $V_{50}$ velocity. However, a corresponding improvement of backface signature reduction with increased fiber strength properties has not been similarly recognized. Accordingly, there is a need in the art for a method to produce ballistic resistant composites having both superior $V_{50}$ ballistic performance as well as low backface signature. The invention provides a solution to this need.

It has been unexpectedly found that there is a direct correlation between backface signature and the tendency of the component fibers of a ballistic resistant composite to delaminate from each other and/or delaminate from fiber surface coatings as a result of a projectile impact. By improving the bond between a fiber surface and a fiber surface coating, the fiber-fiber disengagement and/or fiber-coating delamination effect are reduced, thereby increasing friction on the fibers and increasing projectile engagement with the fibers. Accordingly, the composite structural properties are improved and the energy of a projectile impact is dissipated in a manner that reduces the composite backface deformation.

The invention addresses this need in the art by processing the fibers to improve the bond between a fiber surface and a fiber surface coating prior to uniting the fibers as non-woven fiber layers or fabrics, or prior to weaving fibers into woven fabrics, and prior to coating the fibers with select polymers, as well as prior to merging multiple fiber layers into a multi-ply or multi-layer composite. It has been found that fibrous composites formed from such treated fibers have a dynamic storage modulus that is greater than the dynamic storage modulus of a comparable fibrous composite that has not been similarly treated. Particularly, the fibers are processed to remove at least a portion of the fiber surface finish to expose at least a portion of the fiber surface, thereby allowing a subsequently applied polymer to bond directly with the fiber surface such that the polymer is predominantly in direct contact with the fiber surface rather than predominantly atop the finish. A variety of other fiber treatments may also be conducted to further enhance the ability of a subsequently applied material to adsorb to, adhere to or bond to the fiber surface. The higher dynamic storage modulus reflects increased fiber-fiber bonding within a single fiber ply, increased ply-ply bonding within a single multi-ply fabric or multi-ply fiber layer, and correlates to improved composite structural properties as well as improved composite backface signature.

SUMMARY OF THE INVENTION

The invention provides a process for the dynamic mechanical analysis of a polymeric binder coating on a fiber, the process comprising:

a) providing a first fibrous composite comprising a consolidated plurality of cross-plied fiber plies, each fiber ply comprising a plurality of parallel fibers, each of said fibers having surfaces that are predominantly covered with a fiber surface finish and having a polymeric binder material coating on top of said fiber surface finish wherein said fiber surface finish is between the fiber surfaces and the polymeric binder material;

b) applying an off-axis sinusoidal strain to said first fibrous composite to thereby determine the off-axis dynamic storage modulus of said polymeric binder coating on the fibers of the first fibrous composite, which off-axis sinusoidal strain is applied in a direction that is off-axis from the longitudinal fiber axis of the fibers in each fiber ply;

c) repeating step b) for a second fibrous composite comparable to said first fibrous composite, which second fibrous composite comprises a consolidated plurality of cross-plied fiber plies, each fiber ply comprising a plurality of parallel fibers, each of said fibers having surfaces that are at least partially covered with a polymeric binder material, and wherein said fibers are predominantly free of a fiber surface finish such that said polymeric binder material is predominantly in direct contact with the fiber surfaces;

d) comparing the off-axis dynamic storage modulus of the first fibrous composite with the off-axis dynamic storage modulus of the first fibrous composite to determine which composite has the higher off-axis dynamic storage modulus.

The invention also provides a fibrous composite comprising a plurality of adjoined fiber layers, each fiber layer comprising fibers having surfaces that are at least partially covered with a polymeric material, wherein said fibers are predominantly free of a fiber surface finish such that said polymeric material is predominantly in direct contact with the fiber surfaces; said fibrous composite having a dynamic storage modulus that is greater than the dynamic storage modulus of a comparable fibrous composite having fiber surfaces that are predominantly covered with a fiber surface finish wherein such a fiber surface finish is between the fiber surfaces and the polymeric material.

The invention further provides a method of forming a fibrous composite comprising at least two adjoined fiber layers, each fiber layer comprising fibers having surfaces that are at least partially covered with a polymeric material, wherein said fibers are predominantly free of a fiber surface finish such that said polymeric material is predominantly in direct contact with the fiber surfaces; said composite having a dynamic storage modulus of at least $8.0 \times 10^9$ dyn/cm$^2$ as measured at 25° C. (77° F.), the method comprising providing a plurality of polymeric fibers having surfaces that are predominantly free of a fiber surface finish; optionally treating the fiber surfaces to enhance the surface adsorbability, bonding or adhesion of a subsequently applied polymeric material to the fiber surfaces; applying a polymeric material onto at least a portion of said fibers, thereby adsorbing, bonding or adhering the polymeric material on or to the fiber surfaces; producing a plurality of fiber plies from said fibers either before or after applying said polymeric material to said fibers; and consolidating said plurality of fiber plies to produce a fibrous composite.

DETAILED DESCRIPTION OF THE INVENTION

Backface signature is a measure of the depth of deflection of either soft or hard armor into a backing material or into a user body due to a projectile impact. More specifically, BFS, also known in the art as "backface deformation", "trauma signature" or "blunt force trauma", is a measure of how much impact a projectile leaves under the armor once the armor stops the projectile from penetrating, indicating the potential blunt trauma experienced by the body underneath the armor. The standard method for measuring BFS of soft armor is outlined by NIJ Standard 0101.04, Type IIIA, which identifies a method of transferring the physical deformation of a composite resulting from a non-penetrating projectile impact into a deformable clay backing material held in an open face, box-like fixture. Per the NIJ standard, the armor being tested is secured directly to a front surface of the clay backing and any deformation of the clay resulting from standardized projectile firing conditions is identified and measured. Other methods may be used to measure BFS. The NIJ standard is conventionally used at the present time to evaluate soft armor composites intended for military use.

The terms "backface signature", "backface deformation", "trauma signature" and "blunt force trauma" have the same meaning in the art and are used interchangeably herein. For the purposes of the invention, articles that have superior ballistic penetration resistance describe those which exhibit excellent properties against deformable projectiles, such as bullets, and against penetration of fragments, such as shrapnel. A "fiber layer" as used herein may comprise a single-ply of unidirectionally oriented fibers, a plurality of non-consolidated plies of unidirectionally oriented fibers, a plurality of consolidated plies of unidirectionally oriented fibers, a woven fabric, a plurality of consolidated woven fabrics, or any other fabric structure that has been formed from a plurality of fibers, including felts, mats and other structures, such as those comprising randomly oriented fibers. A "layer" describes a generally planar arrangement. Each fiber layer will have both an outer top surface and an outer bottom surface. A "single-ply" of unidirectionally oriented fibers comprises an arrangement of non-overlapping fibers that are aligned in a unidirectional, substantially parallel array. This type of fiber arrangement is also known in the art as a "unitape", "unidirectional tape", "UD" or "UDT." As used herein, an "array" describes an orderly arrangement of fibers or yarns, which is exclusive of woven fabrics, and a "parallel array" describes an orderly parallel arrangement of fibers or yarns. The term "oriented" as used in the context of "oriented fibers" refers to the alignment of the fibers as opposed to stretching of the fibers. The term "fabric" describes structures that may include one or more fiber plies, with or without molding or consolidation of the plies. For example, a woven fabric or felt may comprise a single fiber ply. A non-woven fabric formed from unidirectional fibers typically comprises a plurality of fiber plies stacked on each other and consolidated. When used herein, a "single-layer" structure refers to any monolithic fibrous structure composed of one or more individual plies or individual layers that have been merged, i.e. consolidated by low pressure lamination or by high pressure molding, into a single unitary structure together with a polymeric binder material. By "consolidating" it is meant that the polymeric binder material together with each fiber ply is combined into a single unitary layer. Consolidation can occur via drying, cooling, heating, pressure or a combination thereof. Heat and/or pressure may not be necessary, as the fibers or fabric layers may just be glued together, as is the case in a wet lamination process. The term "composite" refers to combinations of fibers with at least one polymeric binder material. A "complex composite" as used herein refers to a consolidated combination of a plurality of fiber layers. As described herein, "non-woven" fabrics include all fabric structures that are not formed by weaving. For example, non-woven fabrics may comprise a plurality of unitapes that are at least partially coated with a polymeric binder material, stacked/overlapped and consolidated into a single-layer, monolithic element, as well as a felt or mat comprising non-parallel, randomly oriented fibers that are preferably coated with a polymeric binder composition.

For the purposes of the present invention, a "fiber" is an elongate body the length dimension of which is much greater than the transverse dimensions of width and thickness. The cross-sections of fibers for use in this invention may vary widely, and they may be circular, flat or oblong in cross-section. Thus the term "fiber" includes filaments, ribbons, strips and the like having regular or irregular cross-section, but it is preferred that the fibers have a substantially circular cross-section. As used herein, the term "yarn" is defined as a single strand consisting of multiple fibers. A single fiber may be formed from just one filament or from multiple filaments. A fiber formed from just one filament is referred to herein as either a "single-filament" fiber or a "monofilament" fiber, and a fiber formed from a plurality of filaments is referred to herein as a "multifilament" fiber.

In the context of the present invention, the term "dynamic storage modulus" (E') of a composite is used herein as a measure of the kinetic properties (stress to strain ratio) of a composite when subjected to an oscillating strain at a given frequency and at a given temperature. It has been found that the bond strength of a resin/polymer on a fiber is greater for samples having a greater dynamic storage modulus at a given temperature. Accordingly, resin-fiber bond enhancing treatments may be employed to increase the dynamic storage modulus, and the effectiveness of said treatments may be identified by measuring the dynamic storage modulus.

A preferred method for measuring the dynamic storage modulus of a composite is known as dynamic mechanical analysis. Dynamic mechanical analysis (DMA) is used to determine viscoelastic material properties, such as dynamic storage modulus. To perform a dynamic mechanical analysis, a specimen to be tested is placed in a DMA apparatus, clamped in a holding device within the apparatus and subjected to a dynamic, oscillating strain by a motor in the apparatus. The resulting stress response in the specimen is measured by the transducer in the apparatus. The phase difference between the imposed sinusoidal strain and resultant sinusoidal stress is measured as well. Taking into account the specimen dimensions, this information can be used to determine the dynamic storage modulus of elasticity, or an elastic component (dynamic storage modulus) and a viscous component (loss modulus) of the modulus of elasticity. The dynamic mechanical analysis characterizes the viscoelastic behavior, for example under the influence of temperature, different excitation frequencies, phase changes, or chemical transformation of the specimen. Temperature-dependent measurements may be taken by placing the specimen within a test compartment in which the temperature can be varied. Methods and apparatuses for dynamic mechanical analyses are known, for example, from U.S. Pat. Nos. 5,139,079, 5,710,426, 6,058,784, 6,098,465, 6,146,013, 6,389,906, 6,880,385 the disclosures of which are incorporated herein by reference to the extent consistent herewith. However, these methods and apparatuses are not intended to be limiting, and DMA testing may be conducted using any suitable strain controlled apparatus as would be determined by one skilled in the art, including a Rheometrics Solids Analyzer (RSA II), RSA-G2 analyzer or RSA 3 analyzer available from TA Instruments of New Castle, Del.

The specimens to be subjected to DMA analysis are cut from a fibrous composite comprising either a woven or non-fabric. Such fibrous composites are typically fabricated from a plurality of continuous fibers. When measuring the dynamic storage modulus of a composite of the invention, the composites as tested should comprise or consist of a plurality of adjoined fiber layers/plies, each fiber layer comprising fibers having surfaces that are at least partially covered with a polymeric material. As used herein, adjoined fiber layers may include adjoined unitapes and/or adjoined woven fabrics, and the fiber layers/plies may be adjoined by any conventional technique in the art. Adjoined unitapes are typically arranged in a conventional cross-plied 0°/90° orientation to maximize ballistic penetration resistance (e.g. as determined by standardized $V_{50}$ testing), although this orientation is not mandatory and not necessarily optimal for minimizing backface deformation of a composite. Adjoined unitapes are consolidated using a polymeric binder material as described in greater detail below. Unlike non-woven fabrics, woven fabrics do not require a polymeric binder material to interconnect the component fibers to form a single fiber layer. However, an adhesive or polymeric binder material is generally needed to consolidate or merge multiple woven fiber layers into a multi-layer fibrous composite. Accordingly, it is generally necessary that some form of adhesive or polymeric binder material be present form a composite including at least some woven fabric layers in order to test the dynamic storage modulus of the composite. In a preferred embodiment, woven fabrics are pre-impregnated with a polymeric binder material prior consolidation.

Whether woven or non-woven, when such a polymeric coating is present, it is preferred that the polymeric material coating be strongly bonded to the fibers. It has been unexpectedly found that DMA analysis may be utilized to evaluate the bond strength of the polymer/resin coating on the fibers by applying the dynamic, oscillating strain in a direction that is off-axis from the longitudinal axis of the unidirectional fibers in each fiber layer/fiber ply. When the off-axis dynamic storage modulus is compared with the off-axis dynamic storage modulus of another composite, measured at the same off-axis angle, the composite having the greater fiber-resin bond strength will have the higher dynamic storage modulus.

In this regard, as described in detail below, a "comparable" composite will have the same fiber, the same resin and the same fiber and resin proportions as the composite to which it is compared, with the only difference between the composites being the strength of the bond between the fiber and resin. In this regard, a difference in dynamic storage modulus is indicative of a difference in fiber-to-resin bonding which is affected by the type and extent of fiber surface treatments.

As used herein, "off-axis" sinusoidal strain means a sinusoidal strain that is applied in a direction different than the direction of the longitudinal fiber axis of each fiber ply. In 0°/90° composites where the fibers of adjacent plies are orthogonally oriented with respect to each other, the off-axis angle may be any angle between 0°/90°, including 15°, 30°, 45°, 60°, 75°, etc., where DMA testing is not performed in the direction of greatest fiber tensile strength. The sinusoidal strain is most preferably applied at 45° relative to the longitudinal fiber axis of the fibers in each fiber ply, which would be 45° relative to the fibers in all fiber plies in 0°/90° composites. The variable angle of applied force is accomplished by manipulating the fiber orientation of the specimen. Specifically, whether the specimen is a sample from a woven fabric/fiber layer or a non-woven fabric/multi-ply fiber layer, the sample will comprise fibers having an orthogonal 0°/90° orientation. In a typical woven fabric/fiber layer, the warp fibers are oriented perpendicularly to the weft fibers. In a typical non-woven fabric/fiber layer, unidirectional plies are consolidated where the fibers of each individual ply are oriented perpendicularly)(0°/90° to each other. In a preferred process, a generally rectangular specimen having a width of approximately 6 mm to 8 mm and a length of approximately 40 mm is cut from a larger sample, measuring e.g. 12"×12". The sample is cut on the basis such that the fibers are oriented at 45° relative to the machine and transverse directions. The length of the sample may vary depending on the dimensions of the DMA testing apparatus and the ability to adjust the gap distance between upper and lower clamps. Such would be readily determined by one skilled in the art. Preferred testing is conducted on 4-ply, non-woven unidirectional composites. Testing is preferably conducted at a test frequency of 10 radians/second (rad/s) and at an imposed strain of 0.1%. The sample is then heated, starting at 25° C. and up to 130° C., measuring the dynamic storage modulus (E') at intervals of 1° C. These values may vary as would be determined by one skilled in the art by factors such as size of the tested specimen, geometry of the specimen, span between the end supports, strain rate and temperature, so it is preferred and ideal that all testing factors are kept constant during comparative testing. The temperature of testing is a particularly important factor when testing the dynamic storage modulus of materials incorporating thermoplastic polymers because higher temperatures tend to soften thermoplastic polymers, altering the properties of the material.

In all of the inventive examples illustrated below, dynamic mechanical analysis was performed on composites comprising non-woven fiber layers, measuring the dynamic storage modulus at a range of temperatures as described above. Each composite was formed from a consolidated plurality of 4-ply non-woven fiber layers comprised of a first ply oriented at 0°, a second ply oriented at 90°, a third ply oriented at 0°, and a fourth ply oriented at 90°.

The fibrous composites of the invention are distinguished from other fibrous composites by their greater dynamic storage modulus and a correspondingly superior backface signature performance against high velocity, non-penetrating projectiles. The improvement in the dynamic storage modulus of the fibrous composites of the invention is achieved by, at minimum, at least partially removing a pre-existing fiber surface finish from the fibers prior to processing the fibers into a fabric, wherein forming a fabric includes the fabrication of woven fabric layers, non-woven fabric layers or a non-woven fiber plies. The removal of fiber surface finishes prior to the formation of non-woven fabric layers or non-woven fiber plies, or prior to the weaving of woven fabrics, has not hereinbefore been known because the fiber surface finish is generally known as a necessary processing aid as described above. For example, in the fabrication of non-woven fabrics, a fiber surface finish is generally required to reduce static build-up, prevent fiber tangling, lubricate the fiber to allow it to slide over loom components, and improve fiber cohesion during processing, including during fiber drawing steps.

While fiber surface finishes are typically needed during conventional fabric processing, they generally do not contribute to the final fabric properties. To the contrary, by covering fiber surfaces, the finish interferes with the ability of the fiber surfaces to contact each other, and interferes with the ability of the fiber surfaces to directly adsorb subsequently applied adsorbates, such as liquid or solid resins or polymeric binder materials that are applied onto the fibers, positioning the adsorbates on top of the finish rather than directly on the fiber surfaces. This is problematic. In the former situation, the finish acts as a lubricant on the fiber surfaces and thus reduces friction between adjacent fibers. In the latter situation, the finish prevents subsequently applied materials from bonding directly and strongly to the fiber surfaces, potentially preventing coatings from bonding to fibers altogether, as well as risking delamination during a ballistic impact. To enhance fiber-fiber friction and to permit direct bonding of resins or polymeric binder materials to the fiber surfaces, thereby increasing the fiber-coating bond strength, it is necessary that the existing fiber surface finish be at least partially removed, and preferably substantially completely removed from all or some of the fiber surfaces of some or all of the component fibers forming a fibrous composite.

The at least partial removal of the fiber surface finish will preferably begin once all fiber drawing/stretching steps have been completed. The step of washing the fibers or otherwise removing the fiber finish will remove enough of the fiber finish so that at least some of the underlying fiber surface is exposed, although different removal conditions should be expected to remove different amounts of the finish. For example, factors such as the composition of the washing agent (e.g. water), mechanical attributes of the washing technique (e.g. the force of the water contacting the fiber; agitation of a washing bath, etc.), will affect the amount of finish that is removed. For the purposes herein, minimal processing to achieve minimal removal of the fiber finish will generally expose at least 10% of the fiber surface area. Preferably, the fiber surface finish is removed such that the fibers are predominantly free of a fiber surface finish. As used herein, fibers that are "predominantly free" of a fiber surface finish are fibers which have had at least 50% by weight of their finish removed, more preferably at least about 75% by weight of their finish removed, more preferably at least about 80% by weight of their finish removed. It is even more preferred that the fibers are substantially free of a fiber surface finish. Fibers that are "substantially free" of a fiber finish are fibers which have had at least about 90% by weight of their finish removed, and most preferably at least about 95% by weight of their finish removed, thereby exposing at least about 90% or at least about 95% of the fiber surface area that was previously covered by the fiber surface finish. Most preferably, any residual finish will be present in an amount of less than or equal to about 0.5% by weight based on the weight of the fiber plus the weight of the finish, preferably less than or equal to about 0.4% by weight, more preferably less than or equal to about 0.3% by weight, more preferably less than or equal to about 0.2% by weight and most preferably less than or equal to about 0.1% by weight based on the weight of the fiber plus the weight of the finish.

Depending on the surface tension of the fiber finish composition, a finish may exhibit a tendency to distribute itself over the fiber surface, even if a substantial amount of the finish is removed. Thus, a fiber that is predominantly free of a fiber surface finish may still have a portion of its surface area covered by a very thin coating of the fiber finish. However, this remaining fiber finish will typically exist as residual patches of finish rather than a continuous coating. Accordingly, a fiber having surfaces that are predominantly free of a fiber surface finish preferably has its surface at least partially exposed and not covered by a fiber finish, where preferably less than 50% of the fiber surface area is covered by a fiber surface finish. The fibrous composites of the invention comprising fiber surfaces that are predominantly free of a fiber finish are then coated with a polymeric binder material. Where removal of the fiber finish has resulted in less than 50% of the fiber surface area being covered by a fiber surface finish, the polymeric binder material will thereby be in direct contact with greater than 50% of the fiber surface area.

As a result of such finish removal, fibrous composites of the invention have a dynamic storage modulus that is greater than the dynamic storage modulus of a comparable fibrous composite having fibers that are predominantly covered with a fiber surface finish, e.g. where a fiber surface finish is present between the fiber surfaces and the polymeric material on greater than 50% of the fiber surface area.

Most preferably, the fiber surface finish is substantially completely removed from the fibers and the fiber surfaces are substantially completely exposed. In this regard, a substantially complete removal of the fiber surface finish is the removal of at least about 95%, more preferably at least about 97.5% and most preferably at least about 99.0% removal of the fiber surface finish, and whereby the fiber surface is at least about 95% exposed, more preferably at least about 97.5% exposed and most preferably at least about 99.0% exposed. Ideally, 100% of the fiber surface finish is removed, thereby exposing 100% of the fiber surface area. Following removal of the fiber surface finish, it is also preferred that the fibers are cleared of any removed finish particles prior to application of a polymeric binder material, resin or other adsorbate onto the exposed fiber surfaces.

As used herein, a "comparable" fibrous composite is defined as a composite (theoretical or real) which is identical or substantially similar to a treated composite of the invention where the inventive composite has had at least a portion of the fiber surface finish removed to expose at least a portion of the fiber surface, optionally with additional fiber treatments such as plasma treating or corona treating, and where a polymeric material is accordingly bonded directly to the fiber surface in areas where the finish has been removed. In this regard, "substantially similar" refers to any minimal error experienced when setting the constant factors. In other words, the comparable fibrous composite is a "control composite" to which a "treated composite" of the invention is compared. Particularly, both the control composite and treated composite of the invention will both be fabricated from the same fiber type (same fiber chemistry, tenacity, modulus, etc.), comprise the same fiber layer structure (e.g. woven or non-woven), comprise the same type of polymeric material (also referred to as a binder polymer, polymeric binder material or polymeric matrix) that is coated on the fibers, the same quantity of resin in the composite, the same number of fiber plies/layer, etc. Both the control composite and treated composite will also be formed according to the same consolidation/molding conditions. All factors except for the fiber surface treatments described herein are intended to be kept constant. These are all important considerations because data has shown, for example, that BFS and dynamic storage modulus are dependent to some extent on the type of resin used, just like BFS and dynamic storage modulus are dependent to some extent on the presence of a fiber finish and on the surface treatments of the fiber. The data presented herein supports this premise that a treated composite will exhibit lower BFS and higher dynamic storage modulus properties relative to an identical or substantially similar control composite, not necessarily relative to other composites having elements that are not kept constant. As processing of the fibers to achieve minimal removal of the fiber finish will generally expose at least about 10% of the fiber surface area, a comparable composite which has not been similarly washed or treated to remove at least a portion of the fiber finish will have less than 10% of the fiber surface area exposed, with zero percent surface exposure or substantially no fiber surface exposure.

As previously described, removal of the fiber surface finish enhances fiber-fiber friction as well as the bond strength between the fiber and a subsequently applied coating. Increasing fiber-fiber friction and increasing fiber-coating bond strength has been found to increase projectile engagement with the fibers, thereby improving the dynamic storage modulus of fibrous composites formed from said fibers, as well as improving the ability of fibrous composites formed from said fibers to stop projectiles, and also reducing backface signature resulting from a projectile impact. The improved fiber-coating bond strength also reduces the amount of binder needed to adequately bind the fibers together. This reduction in binder quantity allows a greater number of fibers to be included in a fabric, which allows for potentially producing lighter ballistic materials having improved strength. This also leads to further improved stab resistance of the resulting fabric composites as well as an increased resistance of the composites against repeated impacts.

Any conventionally known method for removing fiber surface finishes is useful within the context of the present invention, including both mechanical and chemical techniques means. The necessary method is generally dependent on the composition of the finish. For example, in the preferred embodiment of the invention, the fibers are coated with a finish that is capable of being washed off with only water. Typically, a fiber finish will comprise a combination of one or more lubricants, one or more non-ionic emulsifiers (surfactants), one or more anti-static agents, one or more wetting and cohesive agents, and one or more antimicrobial compounds. The finish formulations preferred herein can be washed off with only water. Mechanical means may also be employed together with a chemical agent to improve the efficiency of the chemical removal. For example, the efficiency of finish removal using de-ionized water may be enhanced by manipulating the force, direction, velocity, etc. of the water application process.

Most preferably, the fibers are washed and/or rinsed with water as a fiber web, preferably using de-ionized water, with optional drying of the fibers after washing, without using any other chemicals. In other embodiments where the finish is not water soluble, the finish may be removed or washed off with, for example, an abrasive cleaner, chemical cleaner or enzyme cleaner. For example, U.S. Pat. Nos. 5,573,850 and 5,601,775, which are incorporated herein by reference, teach passing yarns through a bath containing a non-ionic surfactant (Hostapur® CX, commercially available from Clariant Corporation of Charlotte, N.C.), trisodium phosphate and sodium hydroxide, followed by rinsing the fibers. Other useful chemical agents non-exclusively include alcohols, such as methanol, ethanol and 2-propanol; aliphatic and aromatic hydrocarbons such as cyclohexane and toluene; chlorinated solvents such as di-chloromethane and tri-chloromethane. Washing the fibers will also remove any other surface contaminants, allowing for more intimate contact between the fiber and resin or other coating material.

The preferred means used to clean the fibers with water is not intended to be limiting except for the ability to substantially remove the fiber surface finish from the fibers. In a preferred method, removal of the finish is accomplished by a process that comprises passing a fiber web through pressurized water nozzles to wash (or rinse) and/or physically remove the finish from the fibers. The fibers may optionally be pre-soaked in a water bath before passing the fibers through said pressurized water nozzles, and/or soaked after passing the fibers through the pressurized water nozzles, and may also optionally be rinsed after any of said optional soaking steps by passing the fibers through additional pressurized water nozzles. The washed/soaked/rinsed fibers are preferably also dried after washing/soaking/rinsing is completed. The equipment and means used for washing the fibers is not intended to be limiting, except that it must be capable of washing individual multifilament fibers/multifilament yarns rather than fabrics, i.e. before they are woven or formed into non-woven fiber layers or plies.

The removal of the fiber surface finish prior to fabric formation is especially intended herein for the production of non-woven fabrics that are formed by consolidating a plurality of fiber plies that comprise a plurality of unidirectionally aligned fibers. In a typical process for forming non-woven unidirectionally aligned fiber plies, fiber bundles are supplied from a creel and led through guides and one or more spreader bars into a collimating comb, followed by coating the fibers with a polymeric binder material. Alternately the fibers can be coated before encountering the spreader bars, or they may be coated between two sets of spreader bars, one before and one after the coating section. A typical fiber bundle (e.g. a yarn) will have from about 30 to about 2000 individual filaments, each fiber typically including, but not limited to, from about 120 to about 240 individual filaments. The spreader bars and collimating comb disperse and spread out the bundled fibers, reorganizing them side-by-side in a coplanar fashion. Ideal fiber spreading results in the individual fibers, or even individual filaments, being positioned next to one another in a single fiber plane, forming a substantially unidirectional, parallel array of fibers with a minimal amount of fibers overlapping each other. Removing the fiber surface finish before or during this spreading step may enhance and accelerate the spreading of the fibers into such a parallel array due to the physical interaction of the cleaning agent (e.g. water) with which the fibers/filaments interact. Following fiber spreading and collimating, the fibers of such a parallel array will typically contain from about 3 to 12 fiber ends per inch (1.2 to 4.7 ends per cm), depending on the fiber thickness. Accordingly, removal of the fiber surface finish achieves a dual benefit of enhancing fiber spreading and improves the bond strength of subsequently applied materials/adsorbates on the fiber surfaces.

While removal of the fiber surface finish alone achieves the aforementioned benefits, even greater results may be achieved by conducting bond enhancing treatments on the fiber surfaces after the at least partial finish removal. In particular, it has been found that backface signature reduction is directly proportional to increases in fiber-fiber friction and fiber-coating bond strength. Treating or modifying the fiber surfaces with a bond enhancing treatment prior to fabric formation has been found to achieve even greater improvements in composite backface signature reduction, particularly when the bond enhancing treatment is combined with washing the fibers to at least partially remove the fiber finish. This is particularly evident when an adsorbate such as a polymeric binder material or resin is applied onto the fiber surfaces, such as a polymeric binder material or resin that is conventionally used for fabrication of non-woven fabrics, or which is applied after weaving fabrics and at least partially removing a fiber surface finish. The stronger the bond of the adsorbate (e.g. polymer/resin) to the fiber surface, the greater the reduction in backface signature. Accordingly, in the most preferred embodiments of the invention, after the at least partial removal of the fiber surface finish, but prior to fabric formation, it is particularly desired to conduct a treatment of the fiber surfaces under conditions effective to enhance the adsorbability/bonding of a subsequently applied adsorbate (e.g. polymer/resin) on the fiber surfaces. Removal of the fiber finish allows these additional processes to act directly on the surface of the fiber and not on the fiber surface finish or on surface contaminants. This is most desired because surface finishes tend to interfere with attempts to treat the surface of the fiber, acting as a barrier or contaminant. Removal of the finish thus also improves the quality and uniformity of subsequent fiber surface treatments. The benefits of finish removal and such further treatments are cumulative, and improvements in backface signature performance should increase with an increased percentage of finish removal and with greater effectiveness of the treatments.

To this end, useful treatments or modifications include anything that is effective to enhance the adsorbability of a subsequently applied adsorbate on the fiber surfaces, where an adsorbate may be any solid, liquid or gas, including polymeric binder materials and resins, and where adsorption includes any form of bonding of the materials to the fiber surfaces. There are various means by which this may be accomplished, including treatments that roughen the surface, add polarity to the surface, oxidize the fiber surface or fiber surface moieties, increase the surface energy of the fiber, reduce the contact angle of the fiber, increase wettability of the fiber, modify the crosslink density of the fiber surface, add a chemical functionality to the fiber surface, ablate the surface, or any other means of improving the interaction between the bulk fiber and fiber surface coatings to improve the anchorage of the coatings to fiber surfaces. This modified interaction can easily be seen in improvements in BFS.

Suitable fiber surface treatments or surface modifications include processes that may be known in the art, such as corona treating the fibers, plasma treating the fibers, plasma coating the fibers, direct fluorination of the fiber surfaces with elemental fluorine, a chemical treatment such as chemical UV grafting, or a surface roughening treatment, such as chromic etching. Also suitable are treatments that are yet undeveloped for large scale application that enhance the ability of an adsorbate to adsorb on or any material to bond with the exposed and treated fiber surfaces following removal fiber surface finish but prior to fabric formation. Each of these exemplary processes, through their action on the surface of the fiber, can be employed to modify, improve or reduce the interaction between the bulk fiber and subsequent coating materials, depending on fiber chemistry. Any combination of these processes can be employed and these sub-processes can be placed in different sequences, although there may be some sequences that are preferred over others depending on various factors, such as fiber type or natural fiber surface properties. The various treatment steps of the invention may be utilized as a recipe for manipulating the fibers in order to place the composite within the desired range for dynamic storage modulus. If dynamic mechanical analysis determines that a particular composite has a lower dynamic storage modulus than desired (e.g. less than $8.0 \times 10^9$ dyn/cm$^2$), that is indicative that further fiber washing and/or further surface treatments (e.g. corona treatment, plasma treatment, etc.) should be conducted to further increase the dynamic storage modulus to fall within the desired range.

The most preferred treatments are corona treatment of the fiber surfaces and plasma treatment of the fiber surfaces. Corona treatment is a process in which a fiber is passed through a corona discharge station, thereby passing the fiber web through a series of high voltage electric discharges, which tend to act on the surface of the fiber web in a variety of ways, including pitting, roughing and introducing polar functional groups by way of partially oxidizing the surface of the fiber. Corona treatment typically oxidizes the fiber surface and/or adds polarity to the fiber surface. Corona treatment also acts by burning small pits or holes into the surface of the fiber. When the fibers are oxidizable, the extent of oxidation is dependent on factors such as power, voltage and frequency of the corona treatment. Residence time within the corona discharge field is also a factor, and this can be manipulated by corona treater design or by the line speed of the process. Suitable corona treatment units are available, for example, from Enercon Industries Corp., Menomonee Falls, Wis., from Sherman Treaters Ltd, Thame, Oxon., UK, or from Softal Corona & Plasma GmbH & Co of Hamburg, Germany.

In a preferred embodiment, the fibers are subjected to a corona treatment of from about 2 Watts/ft$^2$/MIN to about 100 Watts/ft$^2$/MIN, more preferably from about 20 Watts/ft$^2$/MIN to about 50 Watts/ft$^2$/MIN. Lower energy corona treatments from about 1 Watts/ft$^2$/MIN to about 5 Watts/ft$^2$/MIN are also useful may be less effective. In addition to applying a charge to the fiber surface, a corona treatment may roughen the surface by pitting the surface of the fiber.

In a plasma treatment, the fibers, typically as a fiber web, are passed through an ionized atmosphere in a chamber that is filled with an inert or non-inert gas, such as oxygen, argon, helium, ammonia, or another appropriate inert or non-inert gas, including combinations of the above gases, to thereby contact the fibers with an electric discharge. At the fiber surfaces, collisions of the surfaces with charged particles (ions) result in both the transfer of kinetic energy and the exchange of electrons, etc. In addition, collisions between the surfaces and free radicals will result in similar chemical rearrangements. Bombardment of the fiber surface by ultraviolet light that is emitted by excited atoms and molecules relaxing to lower states also causes chemical changes to the fiber substrate.

As a result of these interactions, the plasma treatment may modify both the chemical structure of the fiber as well as the topography of the fiber surfaces. For example, like corona treatment, a plasma treatment may also add polarity to the fiber surface and/or oxidize fiber surface moieties. Plasma treatment may also serve to increase the surface energy of the fiber, reduce the contact angle, modify the crosslink density of the fiber surface, increase the melting point and the mass anchorage of subsequent coatings, and may add a chemical functionality to the fiber surface and potentially ablate the fiber surface. These effects are likewise dependent on the fiber chemistry, and are also dependent on the type of plasma employed.

The selection of gas is important for the desired surface treatment because the chemical structure of the surface is modified differently using different plasma gases. Such would be determined by one skilled in the art. It is known, for example, that amine functionalities may be introduced to a fiber surface using ammonia plasma, while carboxyl and hydroxyl groups may be introduced by using oxygen plasma. Accordingly, the reactive atmosphere may comprise one or more of argon, helium, oxygen, nitrogen, ammonia, and/or other gas known to be suitable for plasma treating of fabrics. The reactive atmosphere may comprise one or more of these gases in atomic, ionic, molecular or free radical form. For example, in a preferred continuous process of the invention, an array of fibers is passed through a controlled reactive atmosphere that preferably comprises argon atoms, oxygen molecules, argon ions, oxygen ions, oxygen free radicals, as well as other trace species. In a preferred embodiment, the reactive atmosphere comprises both argon and oxygen at concentrations of from about 90% to about 95% argon and from about 5% to about 10% oxygen, with 90/10 or 95/5 concentrations of argon/oxygen being preferred. In another preferred embodiment, the reactive atmosphere comprises both helium and oxygen at concentrations of from about 90% to about 95% helium and from about 5% to about 10% oxygen, with 90/10 or 95/5 concentrations of helium/oxygen being preferred. Another useful reactive atmosphere is a zero gas atmosphere, i.e. room air comprising about 79% nitrogen, about 20% oxygen and small amounts of other gases, which is also useful for corona treatment to some extent.

Plasma treating may be conducted in a vacuum chamber or in a chamber maintained at atmospheric conditions. A plasma treatment differs from a corona treatment mainly in that a plasma treatment is conducted in a controlled, reactive atmosphere of gases, whereas in corona treatment the reactive atmosphere is air. The atmosphere in the plasma treater can be easily controlled and maintained, allowing surface polarity to be achieved in a more controllable and flexible manner than corona treating. The electric discharge is by radio frequency (RF) energy which dissociates the gas into electrons, ions, free radicals and metastable products. Electrons and free radicals created in the plasma collide with the fiber surface, rupturing covalent bonds and creating free radicals on the fiber surface. In a batch process, after a predetermined reaction time or temperature, the process gas and RF energy are turned off and the leftover gases and other byproducts are removed. In a continuous process, which is preferred herein, an array of fibers is passed through a controlled reactive atmosphere comprising atoms, molecules, ions and/or free radicals of the selected reactive gases, as well as other trace species. The reactive atmosphere is constantly generated and replenished, likely reaching a steady state composition, and is not turned off or quenched until the coating machine is stopped.

Plasma treatment may be carried out using any useful commercially available plasma treating machine, such as plasma treating machines available from Softal Corona & Plasma GmbH & Co of Hamburg, Germany; 4$^{th}$ State, Inc of Belmont Calif.; Plasmatreat US LP of Elgin Ill.; Enercon Surface Treating Systems of Milwaukee, Wis. A preferred plasma treating process is conducted at about atmospheric pressure, i.e. 1 atm (760 mm Hg (760 torr)), with a chamber temperature of about room temperature (70° F.-72° F.). The temperature inside the plasma chamber may potentially change due to the treating process, but the temperature is generally not independently cooled or heated during treatments, and it is not believed to affect the treatment of the fibers as they rapidly pass through the plasma treater. The temperature between the plasma electrodes and the fiber web is typically approximately 100° C. The plasma treating process is preferably conducted under RF power at about 0.5 kW to about 3.5 kW, more preferably from about 1.0 kW to about 3.05 kW, and most preferably plasma treating is conducted using an atmospheric plasma treater set at 2.0 kW. This power is distributed over the width of the plasma treating zone (or the length of the electrodes) and this power is also distributed over the length of the substrate or fiber web at a rate that is inversely proportional to the line speed at which the fiber web passes through the reactive atmosphere of the plasma treater. This energy per unit area per unit time (watts per square foot per minute or W/SQFT/MIN) or energy flux, is a useful way to compare treatment levels. Effective values for energy flux are preferably from about 0.5 to about 200 Watts/SQFT/MIN, more preferably from about 1 to about 100 Watts/SQFT/MIN, even more preferably from about 1 to about 80 Watts/SQFT/MIN and most preferably from about 2 to about 40 Watts/SQFT/MIN. The total gas flow rate is approximately 16 liters/min, but this is not intended to be strictly limiting. The plasma treatment time (or residence time) of the fiber is approximately 2 seconds, although this is relative to the dimensions of the plasma treater employed and is not intended to be strictly limiting. A more appropriate measure is the amount of plasma treatment in terms of RF power applied to the fiber per unit area over time.

Plasma coating is defined as activating the surface of the fiber web and passing the activated fiber web through an atmosphere containing vinyl monomers, vinyl oligomers or some other reactive species. Plasma coating can add very specific chemical functionality to the surface of the fiber, and can add a different polymeric character to the surface of the fiber. In a direct fluorination treatment, the fiber surfaces are modified by direct fluorination of the fibers with elemental fluorine. For example, the fiber surfaces may be fluorinated by contacting the fiber surfaces with a mixture of 10% $F_2$/90% He at 25° C. to deposit elemental fluorine on said surfaces. The elemental fluorine present on the fiber surfaces serve as functional groups for bonding with subsequently applied coating materials. See also, for example, U.S. Pat. Nos. 3,988,491 and 4,020,223, which are incorporated herein by reference, which teach direct fluorination of fibers using a mixture of elemental fluorine, elemental oxygen and a carrier gas. UV grafting is also a well known process in the art. In an optional process of UV grafting of a ballistic fiber surface, the fibers (or fabric) are soaked in a solution of a monomer, photosensitizer and a solvent to at least partially coat the fiber/fabric surfaces with the monomer and photosensitizer. The coated fibers are then irradiated with UV irradiation, as is well known in the art. The particular selection of monomer type, photosensitizer type and solvent type will vary as desired by and readily determined by one skilled in the art. For example, acrylamide groups may be grafted onto UHMWPE polymer chains via an acrylamide grafting monomer, as discussed in the article entitled, "Studies on surface modification of UHMWPE fibers via UV initiated grafting" by Jieliang Wang, et al. of the Department of Applied Chemistry, School of Science, Northwestern Polytechnical University, Xi'an, Shaanxi 710072, PR China. Applied Surface Science, Volume 253, Issue 2, 15 Nov. 2006, pages 668-673, the disclosure of which is incorporated herein by reference to the extent consistent herein.

Additionally, the fibers of the invention may be treated with one or more than one of these of optional treatments. For example, the fibers may be both roughened by chromic etching and plasma treated, or both corona treated and plasma coated, or both plasma treated and plasma coated. Additionally, composites and fabrics of the invention may comprise some fibers that are treated and some fibers that are not treated. For example, composites herein may be fabricated from some fibers that are corona treated and some fibers that are plasma treated, or some fibers that are fluorinated and some fibers that are not fluorinated.

Each of these treatments will be conducted after the at least partial removal of the fiber surface finish but prior to the application of any binder/matrix resins or other surface adsorbates/coatings. Treating the exposed fiber surfaces immediately before coating the aligned fiber web with a polymeric binder material or resin is most preferred because it will cause the least disruption to the fiber manufacturing process and will leave the fiber in a modified and unprotected state for the shortest period of time. It is ideal to remove the fiber surface finish and treat the exposed fiber surfaces immediately after unwinding fibers from a fiber spool (wound fiber package) and aligning the fibers into a fiber web, followed by immediately coating or impregnating the fibers with a polymer/resin coating. This will also leave the fibers in a treated and uncoated state for the shortest length of time should there be considerations about the shelf-life or decay rate of the surface modification of the fiber. However, this is ideal primarily for causing the least disruption to the overall fabrication process, and not necessarily for achieving an improvement in dynamic storage modulus or BFS performance of the composite.

As a result of the at least partial removal of the fiber finish and optional surface treatments, fibrous composites of the invention comprising a plurality of adjoined fiber layers have a preferred dynamic storage modulus of at least about $8.0 \times 10^9$ dyn/cm$^2$, more preferably at least about $8.5 \times 10^9$ dyn/cm$^2$, more preferably at least about $9.0 \times 10^9$ dyn/cm$^2$, more preferably at least about $9.5 \times 10^9$ dyn/cm$^2$, more preferably at least about $10.0 \times 10^9$ dyn/cm$^2$, more preferably at least about $12.0 \times 10^9$ dyn/cm$^2$, more preferably at least about $15.0 \times 10^9$ dyn/cm$^2$, more preferably at least about $20.0 \times 10^9$ dyn/cm$^2$ and most preferably at least about $25.0 \times 10^9$ dyn/cm$^2$, all being measured at an ambient temperature of 25° C. (77° F.) on a specimen having a width of about 6 mm to about 8 mm, a length of about 40 mm, and thickness of about 0.4 mm, a gap distance between clamps of about 20 mm, a frequency of 10 radians/sec, and at an applied strain of approximately 0.1%, at variable temperatures. These dynamic storage modulus values are relevant to composite samples as tested under said conditions and with the above specified specimen size and shape. Comparative measurements particularly should be made for samples having the same number of component plies/layers or the same thickness or equivalent areal densities. Any comparative measurements must be compared for samples tested at the same testing temperature.

Fibrous composites as described above having said dynamic storage modulus values have been found to exhibit significant lower backface signature relative to composites having inferior dynamic storage modulus than the composites of the invention. This is particularly evident when the component fibers are polyethylene fibers, which are naturally superior than other fibers in their ballistic resistance abilities but have a lower natural affinity for polymer coatings. Treating the surfaces of polyethylene fibers with any combination of the treatments as described above, prior to the fabrication of polyethylene-based fabrics formed therefrom, to increase the dynamic storage modulus of polyethylene-based composites, achieves a combination of structural properties, ballistic penetration resistance and backface signature resistance properties that are comparatively superior to any other fiber type, including aramid fibers.

In this regard, the fibrous composites of the invention have a preferred backface signature of less than about 8 mm as measured for a composite having an areal density of 2.0 psf when impacted with a 124-grain, 9 mm FMJ RN projectile fired at a velocity of from about 427 m/s to about 445 m/s (1430 feet/second (fps))±30 fps). This is not to say that all fibrous composites or articles of the invention will have an areal density of 2.0 psf, nor that all fibrous composites or articles of the invention will have a BFS of 8 mm against such an FMJ RN projectile at said velocity. Such only identifies that composites fabricated according to the processes of the invention are characterized in that when fabricated into a 2.0 psf panel, that 2.0 psf panel will have a BFS of less than about 8 mm against such an FMJ RN projectile at said velocity. It should also be understood that the terms BFS, backface deformation, trauma signature and blunt force trauma are not measures of the depth of depression of the composite due to projectile impact, but rather are measures of the depth of depression in a backing material or into a user body due to projectile impact. This is particularly relevant for the study of hard armor, particularly helmet armor, as helmet BFS is typically tested by placing a prototype helmet on a metallic head form, where the helmet is held on the head form by a suspension system that separates the helmet from the head form by ½ inch (1.27 cm). Sections of the head form are filled with clay, and the depth of depression in those clay areas is measured as the BFS without including the ½ inch spacing depth in the measurement. This is done for the purpose of correlating the laboratory BFS testing with actual BFS experienced by a soldier in field use, where a typical helmet incorporates a typical ½ inch offset from the head, due to helmet interior padding or a suspension system/retention harness. The BFS of soft armor, on the other hand, is conventionally tested by placing the armor directly on the clay surface with no spacing, which is consistent with its position in actual field use. Accordingly, BFS depth measurements are relative to the test method used, and when comparing BFS depth measurements, it is necessary to identify whether or not the test method used required positioning the test sample directly on a backing material or spaced from the backing material. In this regard, BFS testing of the fibrous composites of the invention were all measured with a ½ inch space between the 2.0 psf sample and a clay backing material. In the preferred embodiments of the invention, the fibrous composites of the invention have a more preferred backface signature of less than about 7 mm when impacted with a 124-grain, 9 mm FMJ projectile fired at a velocity of from about 427 m/s to about 445 m/s under the projectile firing conditions of NIJ Standard 0101.04, more preferably less than about 6 mm, more preferably less than about 5 mm, more preferably less than about 4 mm, more preferably less than about 3 mm, more preferably less than about 2 mm, and most preferably have a backface signature of less than about 1 mm when impacted with a 124-grain, 9 mm FMJ RN projectile (a bullet comprising approximately 90% copper and 10% zinc excluding the base) fired at a velocity of from about 427 m/s to about 445 m/s. Testing BFS against a 124-grain, 9 mm FMJ RN projectile fired at a velocity of from about 427 m/s to about 445 m/s is common in the art.

Said fibrous composites achieving these BFS values each comprise a plurality of adjoined fiber layers, each fiber layer comprising fibers having surfaces that are at least partially covered with a polymeric material, wherein said fibers are predominantly free of a fiber surface finish such that said polymeric material is predominantly in direct contact with the fiber surfaces, and have a dynamic storage modulus at an ambient temperature of 25° C. (77° F.) of at least about $8.0 \times 10^9$ dyn/cm$^2$, more preferably at least about $8.5 \times 10^9$ dyn/cm$^2$, more preferably at least about $9.0 \times 10^9$ dyn/cm$^2$, more preferably at least about $9.5 \times 10^9$ dyn/cm$^2$, more preferably at least about $10.0 \times 10^9$ dyn/cm$^2$, more preferably at least about $12.0 \times 10^9$ dyn/cm$^2$, more preferably at least about $15.0 \times 10^9$ dyn/cm$^2$, more preferably at least about $20.0 \times 10^9$ dyn/cm$^2$ and most preferably at least about $25.0 \times 10^9$ dyn/cm$^2$ as tested on a sample having the aforementioned dimensions. Said fibrous composites achieving both these BFS values and such dynamic storage modulus properties also preferably exhibit a $V_{50}$ against a 17-grain fragment simulating projectile (FSP) of at least about 1750 feet/sec (fps) (533.40 m/s), more preferably at least about 1800 fps (548.64 m/s), even more preferably at least about 1850 fps (563.88 m/s) and most preferably at least about 1900 fps (579.12 m/s). All of the above $V_{50}$ values are for armor panels having a composite areal density of approximately 1.0 lbs/ft$^2$ (psf)(4.88 kg/m$^2$ (ksm)). All of the above BFS values are for armor panels having a composite areal density of approximately 2.0 lbs/ft$^2$ (psf)(7.96 kg/m$^2$ (ksm)). As with BFS, this is not to say that all fibrous composites or articles of the invention will have a particular areal density, nor that all fibrous composites or articles of the invention will have a $V_{50}$ against a 17-grain FSP of at least about 1750 feet/sec. Such only identifies that composites fabricated according to the processes of the invention are characterized in that when fabricated into a 1.0 psf panel, that 1.0 psf panel will have a $V_{50}$ against a 17-grain FSP of at least about 1750 feet/sec.

The fiber layers and composites formed herein are preferably ballistic resistant composites formed from high-strength, high tensile modulus polymeric fibers. Most preferably, the fibers comprise high strength, high tensile modulus fibers which are useful for the formation of ballistic resistant materials and articles. As used herein, a "high-strength, high tensile modulus fiber" is one which has a preferred tenacity of at least about 7 g/denier or more, a preferred tensile modulus of at least about 150 g/denier or more, and preferably an energy-to-break of at least about 8 J/g or more, each both as measured by ASTM D2256. As used herein, the term "denier" refers to the unit of linear density, equal to the mass in grams per 9000 meters of fiber or yarn. As used herein, the term "tenacity" refers to the tensile stress expressed as force (grams) per unit linear density (denier) of an unstressed specimen. The "initial modulus" of a fiber is the property of a material representative of its resistance to deformation. The term "tensile modulus" refers to the ratio of the change in tenacity, expressed in grams-force per denier (g/d) to the change in strain, expressed as a fraction of the original fiber length (in/in).

The polymers forming the fibers are preferably high-strength, high tensile modulus fibers suitable for the manufacture of ballistic resistant composites/fabrics. Particularly suitable high-strength, high tensile modulus fiber materials that are particularly suitable for the formation of ballistic resistant composites and articles include polyolefin fibers, including high density and low density polyethylene. Particularly preferred are extended chain polyolefin fibers, such as highly oriented, high molecular weight polyethylene fibers, particularly ultra-high molecular weight polyethylene fibers, and polypropylene fibers, particularly ultra-high molecular weight polypropylene fibers. Also suitable are aramid fibers, particularly para-aramid fibers, polyamide fibers, polyethylene terephthalate fibers, polyethylene naphthalate fibers, extended chain polyvinyl alcohol fibers, extended chain polyacrylonitrile fibers, polybenzazole fibers, such as polybenzoxazole (PBO) and polybenzothiazole (PBT) fibers, liquid crystal copolyester fibers and other rigid rod fibers such as M5® fibers. Each of these fiber types is conventionally known in the art. Also suitable for producing polymeric fibers are copolymers, block polymers and blends of the above materials.

The most preferred fiber types for ballistic resistant fabrics include polyethylene, particularly extended chain polyethylene fibers, aramid fibers, polybenzazole fibers, liquid crystal copolyester fibers, polypropylene fibers, particularly highly oriented extended chain polypropylene fibers, polyvinyl alcohol fibers, polyacrylonitrile fibers and other rigid rod fibers, particularly M5® fibers. Specifically most preferred fibers are aramid fibers.

In the case of polyethylene, preferred fibers are extended chain polyethylenes having molecular weights of at least 500,000, preferably at least one million and more preferably between two million and five million. Such extended chain polyethylene (ECPE) fibers may be grown in solution spinning processes such as described in U.S. Pat. Nos. 4,137,394 or 4,356,138, which are incorporated herein by reference, or may be spun from a solution to form a gel structure, such as described in U.S. Pat. Nos. 4,551,296 and 5,006,390, which are also incorporated herein by reference. A particularly preferred fiber type for use in the invention are polyethylene fibers sold under the trademark SPECTRA® from Honeywell International Inc. SPECTRA® fibers are well known in the art and are described, for example, in U.S. Pat. Nos. 4,623,547 and 4,748,064. In addition to polyethylene, another useful polyolefin fiber type is polypropylene (fibers or tapes), such as TEGRIS® fibers commercially available from Milliken & Company of Spartanburg, S.C.

Also particularly preferred are aramid (aromatic polyamide) or para-aramid fibers. Such are commercially available and are described, for example, in U.S. Pat. No. 3,671,542. For example, useful poly(p-phenylene terephthalamide) filaments are produced commercially by DuPont under the trademark of KEVLAR®. Also useful in the practice of this invention are poly(m-phenylene isophthalamide) fibers produced commercially by DuPont under the trademark NOMEX® and fibers produced commercially by Teijin under the trademark TWARON®; aramid fibers produced commercially by Kolon Industries, Inc. of Korea under the trademark HERACRON®; p-aramid fibers SVM™ and RUSAR™ which are produced commercially by Kamensk Volokno JSC of Russia and ARMOS™ p-aramid fibers produced commercially by JSC Chim Volokno of Russia.

Suitable polybenzazole fibers for the practice of this invention are commercially available and are disclosed for example in U.S. Pat. Nos. 5,286,833, 5,296,185, 5,356,584, 5,534,205 and 6,040,050, each of which is incorporated herein by reference. Suitable liquid crystal copolyester fibers for the practice of this invention are commercially available and are disclosed, for example, in U.S. Pat. Nos. 3,975,487; 4,118,372 and 4,161,470, each of which is incorporated herein by reference. Suitable polypropylene fibers include highly oriented extended chain polypropylene (ECPP) fibers as described in U.S. Pat. No. 4,413,110, which is incorporated herein by reference. Suitable polyvinyl alcohol (PV-OH) fibers are described, for example, in U.S. Pat. Nos. 4,440,711 and 4,599,267 which are incorporated herein by reference. Suitable polyacrylonitrile (PAN) fibers are disclosed, for example, in U.S. Pat. No. 4,535,027, which is incorporated herein by reference. Each of these fiber types is conventionally known and is widely commercially available.

M5® fibers are formed from pyridobisimidazole-2,6-diyl (2,5-dihydroxy-p-phenylene) and are manufactured by Magellan Systems International of Richmond, Va. and are described, for example, in U.S. Pat. Nos. 5,674,969, 5,939,553, 5,945,537, and 6,040,478, each of which is incorporated herein by reference. Also suitable are combinations of all the above materials, all of which are commercially available. For example, the fibrous layers may be formed from a combination of one or more of aramid fibers, UHMWPE fibers (e.g. SPECTRA® fibers), carbon fibers, etc., as well as fiberglass and other lower-performing materials. However, BFS and $V_{50}$ values may vary by fiber type.

The fibers may be of any suitable denier, such as, for example, 50 to about 3000 denier, more preferably from about 200 to 3000 denier, still more preferably from about 650 to about 2000 denier, and most preferably from about 800 to about 1500 denier. The selection is governed by considerations of ballistic effectiveness and cost. Finer fibers are more costly to manufacture and to weave, but can produce greater ballistic effectiveness per unit weight.

As stated above, a high-strength, high tensile modulus fiber is one which has a preferred tenacity of about 7 g/denier or more, a preferred tensile modulus of about 150 g/denier or more and a preferred energy-to-break of about 8 J/g or more, each as measured by ASTM D2256. In the preferred embodiment of the invention, the tenacity of the fibers should be about 15 g/denier or more, preferably about 20 g/denier or more, more preferably about 25 g/denier, still more preferably about 30 g/denier or more, still more preferably about 37 g/denier or more still more preferably about 40 g/denier or more still more preferably about 45 g/denier or more still more preferably about 50 g/denier or more still more preferably about 55 g/denier or more and most preferably about 60 g/denier or more. Preferred fibers also have a preferred tensile modulus of about 300 g/denier or more, more preferably about 400 g/denier or more, more preferably about 500 g/denier or more, more preferably about 1,000 g/denier or more and most preferably about 1,500 g/denier or more. Preferred fibers also have a preferred energy-to-break of about 15 J/g or more, more preferably about 25 J/g or more, more preferably about 30 J/g or more and most preferably have an energy-to-break of about 40 J/g or more. These combined high strength properties are obtainable by employing well known processes. U.S. Pat. Nos. 4,413,110, 4,440,711, 4,535,027, 4,457,985, 4,623,547 4,650,710 and 4,748,064 generally discuss the formation of preferred high strength, extended chain polyethylene fibers. Such methods, including solution grown or gel fiber processes, are well known in the art. Methods of forming each of the other preferred fiber types, including para-aramid fibers, are also conventionally known in the art, and the fibers are commercially available. The fibrous composites of the invention also preferably comprise fibers having a fiber areal density of about 1.7 g/cm³ or less.

After removing at least a portion of the fiber surface finish from the fiber surfaces as desired, and after the fiber surfaces are optionally treated under conditions effective to enhance the adsorbability of a subsequently applied adsorbate on the fiber surfaces, an adsorbate is then optionally applied onto at least a portion of at least some of the fibers. As used herein, the term "adsorption" (or "adsorbability" or "adsorb") is broadly intended to encompass both physisorption and chemisorption of any material (solid, liquid, gas or plasma) on the fiber surface, where "physisorption" is defined herein as physical bonding of a material on a fiber surface and "chemisorption" is defined herein as chemical bonding of a material on a fiber surface, where a chemical reaction occurs at the exposed fiber (i.e. the adsorbant) surface. The term "adsorption" as used herein is intended to include any possible means of attaching, adhering or bonding a material to a substrate surface, physically or chemically, without limitation, including means for increasing fiber wetting/adhesion of fibers in polymer matrices. This expressly includes the adhesion or coating of any solid, liquid or gas material on the fiber surfaces, including any monomer, oligomer, polymer or resin, and including the application of any organic material or inorganic material onto the fiber surfaces. In this regard, the definition of "adsorbate" is also not intended to be limiting and expressly includes all polymers useful as polymer binder materials, resins or polymeric matrix materials. However, for the purposes of this invention, the class of useful adsorbates expressly excludes materials that do not have binding properties, including fiber surface finish substances such as a spin finish materials, which are not binder materials having binding properties and which, to the contrary, are specifically removed from fiber surfaces according to the invention.

For the purposes of the invention, the application of a polymer binder material adsorbate, such as a resin, is required to achieve a composite having the desired dynamic storage modulus. Accordingly, the fibers forming the woven or non-woven fabrics of the invention are coated with or impregnated with a polymeric binder material. The polymeric binder material either partially or substantially coats the individual fibers of the fiber layers, preferably substantially coating each of the individual fibers of each fiber layer. The polymeric binder material is also commonly known in the art as a "polymeric matrix" material, and these terms are used interchangeably herein. These terms are conventionally known in the art and describe a material that binds fibers together either by way of its inherent adhesive characteristics or after being subjected to well known heat and/or pressure conditions. Such a "polymeric matrix" or "polymeric binder" material may also provide a fabric with other desirable properties, such as abrasion resistance and resistance to deleterious environmental conditions, so it may be desirable to coat the fibers with such a binder material even when its binding properties are not important, such as with woven fabrics.

Suitable polymeric binder materials include both low modulus, elastomeric materials and high modulus, rigid materials. As used herein throughout, the term tensile modulus means the modulus of elasticity as measured by ASTM 2256 for a fiber and by ASTM D638 for a polymeric binder material. A low or high modulus binder may comprise a variety of polymeric and non-polymeric materials. A preferred polymeric binder comprises a low modulus elastomeric material. For the purposes of this invention, a low modulus elastomeric material has a tensile modulus measured at about 6,000 psi (41.4 MPa) or less according to ASTM D638 testing procedures. A low modulus polymer preferably has, the tensile modulus of the elastomer is about 4,000 psi (27.6 MPa) or less, more preferably about 2400 psi (16.5 MPa) or less, more preferably 1200 psi (8.23 MPa) or less, and most preferably is about 500 psi (3.45 MPa) or less. The glass transition temperature (Tg) of the elastomer is preferably less than about 0° C., more preferably the less than about −40° C., and most preferably less than about −50° C. The elastomer also has a preferred elongation to break of at least about 50%, more preferably at least about 100% and most preferably has an elongation to break of at least about 300%.

A wide variety of materials and formulations having a low modulus may be utilized as the polymeric binder. Representative examples include polybutadiene, polyisoprene, natural rubber, ethylene-propylene copolymers, ethylene-propylene-diene terpolymers, polysulfide polymers, polyurethane elastomers, chlorosulfonated polyethylene, polychloroprene, plasticized polyvinylchloride, butadiene acrylonitrile elastomers, poly(isobutylene-co-isoprene), polyacrylates, polyesters, polyethers, fluoroelastomers, silicone elastomers, copolymers of ethylene, polyamides (useful with some fiber types), acrylonitrile butadiene styrene, polycarbonates, and combinations thereof, as well as other low modulus polymers and copolymers curable below the melting point of the fiber.

Also preferred are blends of different elastomeric materials, or blends of elastomeric materials with one or more thermoplastics.

Particularly useful are block copolymers of conjugated dienes and vinyl aromatic monomers. Butadiene and isoprene are preferred conjugated diene elastomers. Styrene, vinyl toluene and t-butyl styrene are preferred conjugated aromatic monomers. Block copolymers incorporating polyisoprene may be hydrogenated to produce thermoplastic elastomers having saturated hydrocarbon elastomer segments. The polymers may be simple tri-block copolymers of the type A-B-A, multi-block copolymers of the type $(AB)_n$ (n=2-10) or radial configuration copolymers of the type $R-(BA)_x$ (x=3-150); wherein A is a block from a polyvinyl aromatic monomer and B is a block from a conjugated diene elastomer. Many of these polymers are produced commercially by Kraton Polymers of Houston, Tex. and described in the bulletin "Kraton Thermoplastic Rubber", SC-68-81. Also useful are resin dispersions of styrene-isoprene-styrene (SIS) block copolymer sold under the trademark PRINLIN® and commercially available from Henkel Technologies, based in Düsseldorf, Germany. Particularly preferred low modulus polymeric binder polymers comprise styrenic block copolymers sold under the trademark KRATON® commercially produced by Kraton Polymers. A particularly preferred polymeric binder material comprises a polystyrene-polyisoprene-polystyrene-block copolymer sold under the trademark KRATON®.

While low modulus polymeric matrix binder materials are most useful for the formation of flexible armor, such as ballistic resistant vests, high modulus, rigid materials useful for forming hard armor articles, such as helmets, are particularly preferred herein. Preferred high modulus, rigid materials generally have a higher initial tensile modulus than 6,000 psi. Preferred high modulus, rigid polymeric binder materials useful herein include polyurethanes (both ether and ester based), epoxies, polyacrylates, phenolic/polyvinyl butyral (PVB) polymers, vinyl ester polymers, styrene-butadiene block copolymers, as well as mixtures of polymers such as vinyl ester and diallyl phthalate or phenol formaldehyde and polyvinyl butyral. A particularly preferred rigid polymeric binder material for use in this invention is a thermosetting polymer, preferably soluble in carbon-carbon saturated solvents such as methyl ethyl ketone, and possessing a high tensile modulus when cured of at least about $1 \times 10^6$ psi (6895 MPa) as measured by ASTM D638. Particularly preferred rigid polymeric binder materials are those described in U.S. Pat. No. 6,642,159, the disclosure of which is incorporated herein by reference. The polymeric binder, whether a low modulus material or a high modulus material, may also include fillers such as carbon black or silica, may be extended with oils, or may be vulcanized by sulfur, peroxide, metal oxide or radiation cure systems as is well known in the art.

Most specifically preferred are polar resins or polar polymers, particularly polyurethanes within the range of both soft and rigid materials at a tensile modulus ranging from about 2,000 psi (13.79 MPa) to about 8,000 psi (55.16 MPa). Preferred polyurethanes are applied as aqueous polyurethane dispersions that are most preferably, but not necessarily, cosolvent free. Such includes aqueous anionic polyurethane dispersions, aqueous cationic polyurethane dispersions and aqueous nonionic polyurethane dispersions. Particularly preferred are aqueous anionic polyurethane dispersions; aqueous aliphatic polyurethane dispersions, and most preferred are aqueous anionic, aliphatic polyurethane dispersions, all of which are preferably cosolvent free dispersions. Such includes aqueous anionic polyester-based polyurethane dispersions; aqueous aliphatic polyester-based polyurethane dispersions; and aqueous anionic, aliphatic polyester-based polyurethane dispersions, all of which are preferably cosolvent free dispersions. Such also includes aqueous anionic polyether polyurethane dispersions; aqueous aliphatic polyether-based polyurethane dispersions; and aqueous anionic, aliphatic polyether-based polyurethane dispersions, all of which are preferably cosolvent free dispersions. Similarly preferred are all corresponding variations (polyester-based; aliphatic polyester-based; polyether-based; aliphatic polyether-based, etc.) of aqueous cationic and aqueous nonionic dispersions. Most preferred is an aliphatic polyurethane dispersion having a modulus at 100% elongation of about 700 psi or more, with a particularly preferred range of 700 psi to about 3000 psi. More preferred are aliphatic polyurethane dispersions having a modulus at 100% elongation of about 1000 psi or more, and still more preferably about 1100 psi or more. Most preferred is an aliphatic, polyether-based anionic polyurethane dispersion having a modulus of 1000 psi or more, preferably 1100 psi or more.

The rigidity, impact and ballistic properties of the articles formed from the composites of the invention are affected by the tensile modulus of the polymeric binder polymer coating the fibers. For example, U.S. Pat. No. 4,623,574 discloses that fiber reinforced composites constructed with elastomeric matrices having tensile moduli less than about 6,000 psi (41,300 kPa) have superior ballistic properties compared both to composites constructed with higher modulus polymers, and also compared to the same fiber structure without a polymeric binder material. However, low tensile modulus polymeric binder material polymers also yield lower rigidity composites. Further, in certain applications, particularly those where a composite must function in both anti-ballistic and structural modes, there is needed a superior combination of ballistic resistance and rigidity. Accordingly, the most appropriate type of polymeric binder polymer to be used will vary depending on the type of article to be formed from the composites of the invention. In order to achieve a compromise in both properties, a suitable polymeric binder may combine both low modulus and high modulus materials to form a single polymeric binder.

The polymeric binder material may be applied either simultaneously or sequentially to a plurality of fibers arranged as a fiber web (e.g. a parallel array or a felt) to form a coated web, applied to a woven fabric to form a coated woven fabric, or as another arrangement, to thereby impregnate the fiber layers with the binder. As used herein, the term "impregnated with" is synonymous with "embedded in" as well as "coated with" or otherwise applied with the coating where the binder material diffuses into the fiber layer and is not simply on a surface of the fiber layers. The polymeric material may also be applied onto at least one array of fibers that is not part of a fiber web, followed by weaving the fibers into a woven fabric or followed by formulating a non-woven fabric following the methods described previously herein. Techniques of forming woven and non-woven fiber plies, layers and fabrics are well known in the art.

Although not required, fibers forming woven fiber layers are at least partially coated with a polymeric binder, followed by a consolidation step similar to that conducted with non-woven fiber layers. Such a consolidation step may be conducted to merge multiple woven fiber layers with each other, or to further merge the binder with the fibers of said woven fabric. For example, a plurality of woven fiber layers do not necessarily have to be consolidated, and may be attached by other means, such as with a conventional adhesive, or by stitching.

Generally, a polymeric binder coating is necessary to efficiently merge, i.e. consolidate, a plurality of non-woven fiber plies. The polymeric binder material may be applied onto the entire surface area of the individual fibers or only onto a partial surface area of the fibers. Most preferably, the coating of the polymeric binder material is applied onto substantially all the surface area of each individual fiber forming a fiber layer of the invention. Where a fiber layer comprises a plurality of yarns, each fiber forming a single strand of yarn is preferably coated with the polymeric binder material.

Any appropriate application method may be utilized to apply the polymeric binder material and the term "coated" is not intended to limit the method by which it is applied onto the filaments/fibers. The polymeric binder material is applied directly onto the fiber surfaces using any appropriate method that would be readily determined by one skilled in the art, and the binder then typically diffuses into the fiber layer as discussed herein. For example, the polymeric binder materials may be applied in solution, emulsion or dispersion form by spraying, extruding or roll coating a solution of the polymer material onto fiber surfaces, wherein a portion of the solution comprises the desired polymer or polymers and a portion of the solution comprises a solvent capable of dissolving or dispersing the polymer or polymers, followed by drying. Alternately, the polymeric binder material may be extruded onto the fibers using conventionally known techniques, such as through a slot-die, or through other techniques such as direct gravure, Meyer rod and air knife systems, which are well known in the art. Another method is to apply a neat polymer of the binder material onto fibers either as a liquid, a sticky solid or particles in suspension or as a fluidized bed. Alternatively, the coating may be applied as a solution, emulsion or dispersion in a suitable solvent which does not adversely affect the properties of fibers at the temperature of application. For example, the fibers can be transported through a solution of the polymeric binder material to substantially coat the fibers and then dried.

In another coating technique, the fibers may be dipped into a bath of a solution containing the polymeric binder material dissolved or dispersed in a suitable solvent, and then dried through evaporation or volatilization of the solvent. This method preferably at least partially coats each individual fiber with the polymeric material, preferably substantially coating or encapsulating each of the individual fibers and covering all or substantially all of the filament/fiber surface area with the polymeric binder material. The dipping procedure may be repeated several times as required to place a desired amount of polymer material onto the fibers.

Other techniques for applying a coating to the fibers may be used, including coating of a gel fiber precursor when appropriate, such as by passing the gel fiber through a solution of the appropriate coating polymer under conditions to attain the desired coating. Alternatively, the fibers may be extruded into a fluidized bed of an appropriate polymeric powder.

While it is necessary that the fibers be coated with a polymeric binder after the at least partial removal of the fiber surface finish, and preferably after a surface treatment that enhances the adsorbability of a subsequently applied adsorbate on the fiber surfaces, the fibers may be coated with the polymeric binder either before or after the fibers are arranged into one or more plies/layers, or before or after the fibers are woven into a woven fabric. Woven fabrics may be formed using techniques that are well known in the art using any fabric weave, such as plain weave, crowfoot weave, basket weave, satin weave, twill weave and the like. Either prior to or after weaving, the individual fibers of each woven fabric material may or may not be coated with the polymeric binder material. Typically, weaving of fabrics is performed prior to coating fibers with the polymeric binder, where the woven fabrics are thereby impregnated with the binder. However, the invention is not intended to be limited by the stage at which the polymeric binder is applied to the fibers, nor by the means used to apply the polymeric binder.

Methods for the production of non-woven fabrics are well known in the art. In the preferred embodiments herein, a plurality of fibers are arranged into at least one array, typically being arranged as a fiber web comprising a plurality of fibers aligned in a substantially parallel, unidirectional array. As previously stated, in a typical process for forming non-woven unidirectionally aligned fiber plies, fiber bundles are supplied from a creel and led through guides and one or more spreader bars into a collimating comb, followed by coating the fibers with a polymeric binder material. A typical fiber bundle will have from about 30 to about 2000 individual fibers. The spreader bars and collimating comb disperse and spread out the bundled fibers, reorganizing them side-by-side in a coplanar fashion. Ideal fiber spreading results in the individual filaments or individual fibers being positioned next to one another in a single fiber plane, forming a substantially unidirectional, parallel array of fibers without fibers overlapping each other. At this point, removing the fiber surface finish before or during this spreading step may enhance and accelerate the spreading of the fibers into such a parallel array.

After the fibers are coated with the binder material, the coated fibers are formed into non-woven fiber layers that comprise a plurality of overlapping, non-woven fiber plies that are consolidated into a single-layer, monolithic element. In a preferred non-woven fabric structure of the invention, a plurality of stacked, overlapping unitapes are formed wherein the parallel fibers of each single ply (unitape) are positioned orthogonally to the parallel fibers of each adjacent single ply relative to the longitudinal fiber direction of each single ply. The stack of overlapping non-woven fiber plies is consolidated under heat and pressure, or by adhering the coatings of individual fiber plies, to form a single-layer, monolithic element which has also been referred to in the art as a single-layer, consolidated network where a "consolidated network" describes a consolidated (merged) combination of fiber plies with the polymeric matrix/binder. Articles of the invention may also comprise hybrid consolidated combinations of woven fabrics and non-woven fabrics, as well as combinations of non-woven fabrics formed from unidirectional fiber plies and non-woven felt fabrics.

Most typically, non-woven fiber layers or fabrics include from 1 to about 6 plies, but may include as many as about 10 to about 20 plies as may be desired for various applications. The greater the number of plies translates into greater ballistic resistance, but also greater weight. Accordingly, the number of fiber plies forming a fiber layer composite and/or fabric composite or an article of the invention varies depending upon the ultimate use of the fabric or article. For example, in body armor vests for military applications, in order to form an article composite that achieves a desired 1.0 pound per square foot or less areal density (4.9 kg/m$^2$), a total of about 100 plies (or layers) to about 50 individual plies (or layers) may be required, wherein the plies/layers may be woven, knitted, felted or non-woven fabrics (with parallel oriented fibers or other arrangements) formed from the high-strength fibers described herein. In another embodiment, body armor vests for law enforcement use may have a number of plies/layers based on the NIJ threat level. For example, for an NIJ Threat Level IIIA vest, there may be a total of 40 plies. For a lower NIJ Threat Level, fewer plies/layers may be employed. The invention allows for the incorporation of a greater number of fiber plies to achieve the desired level of ballistic protection without increasing the fabric weight as compared to other known ballistic resistant structures.

As is conventionally known in the art, excellent ballistic resistance is achieved when individual fiber plies are cross-plied such that the fiber alignment direction of one ply is rotated at an angle with respect to the fiber alignment direction of another ply. Most preferably, the fiber plies are cross-plied orthogonally at 0° and 90° angles, but adjacent plies can be aligned at virtually any angle between about 0° and about 90° with respect to the longitudinal fiber direction of another ply. For example, a five ply non-woven structure may have plies oriented at a 0°/45°/90°/45°/0° or at other angles. Such rotated unidirectional alignments are described, for example, in U.S. Pat. Nos. 4,457,985; 4,748,064; 4,916,000; 4,403,012; 4,623,574; and 4,737,402, all of which are incorporated herein by reference to the extent not incompatible herewith.

Methods of consolidating fiber plies to form fiber layers and composites are well known, such as by the methods described in U.S. Pat. No. 6,642,159. Consolidation can occur via drying, cooling, heating, pressure or a combination thereof. Heat and/or pressure may not be necessary, as the fibers or fabric layers may just be glued together, as is the case in a wet lamination process. Typically, consolidation is done by positioning the individual fiber plies on one another under conditions of sufficient heat and pressure to cause the plies to combine into a unitary fabric. Consolidation may be done at temperatures ranging from about 50° C. to about 175° C., preferably from about 105° C. to about 175° C., and at pressures ranging from about 5 psig (0.034 MPa) to about 2500 psig (17 MPa), for from about 0.01 seconds to about 24 hours, preferably from about 0.02 seconds to about 2 hours. When heating, it is possible that the polymeric binder coating can be caused to stick or flow without completely melting. However, generally, if the polymeric binder material (if it is one that is capable of melting) is caused to melt, relatively little pressure is required to form the composite, while if the binder material is only heated to a sticking point, more pressure is typically required. As is conventionally known in the art, consolidation may be conducted in a calender set, a flat-bed laminator, a press or in an autoclave. Most commonly, a plurality of orthogonal fiber webs are "glued" together with the binder polymer and run through a flat bed laminator to improve the uniformity and strength of the bond. Further, the consolidation and polymer application/bonding steps may comprise two separate steps or a single consolidation/lamination step.

Alternately, consolidation may be achieved by molding under heat and pressure in a suitable molding apparatus. Generally, molding is conducted at a pressure of from about 50 psi (344.7 kPa) to about 5,000 psi (34,470 kPa), more preferably from about 100 psi (689.5 kPa) to about 3,000 psi (20,680 kPa), most preferably from about 150 psi (1,034 kPa) to about 1,500 psi (10,340 kPa). Molding may alternately be conducted at higher pressures of from about 5,000 psi (34,470 kPa) to about 15,000 psi (103,410 kPa), more preferably from about 750 psi (5,171 kPa) to about 5,000 psi, and more preferably from about 1,000 psi to about 5,000 psi. The molding step may take from about 4 seconds to about 45 minutes. Preferred molding temperatures range from about 200° F. (~93° C.) to about 350° F. (~177° C.), more preferably at a temperature from about 200° F. to about 300° F. and most preferably at a temperature from about 200° F. to about 280° F. The pressure under which the fiber layers and fabric composites of the invention are molded typically has a direct effect on the stiffness or flexibility of the resulting molded product. Molding at a higher pressure generally produces stiffer materials, up to a certain limit. In addition to the molding pressure, the quantity, thickness and composition of the fiber plies and polymeric binder coating type also directly affects the stiffness of the articles formed from the composites.

While each of the molding and consolidation techniques described herein are similar, each process is different. Particularly, molding is a batch process and consolidation is a generally continuous process. Further, molding typically involves the use of a mold, such as a shaped mold or a match-die mold when forming a flat panel, and does not necessarily result in a planar product. Normally consolidation is done in a flat-bed laminator, a calendar nip set or as a wet lamination to produce soft (flexible) body armor fabrics. Molding is typically reserved for the manufacture of hard armor, e.g. rigid plates. In either process, suitable temperatures, pressures and times are generally dependent on the type of polymeric binder coating materials, polymeric binder content, process used and fiber type.

To produce a fabric article having sufficient ballistic resistance properties, the total weight of the binder/matrix coating preferably comprises from about 2% to about 50% by weight, more preferably from about 5% to about 30%, more preferably from about 7% to about 20%, and most preferably from about 11% to about 16% by weight of the fibers plus the weight of the coating, wherein 16% is most preferred for non-woven fabrics. A lower binder/matrix content is appropriate for woven fabrics, wherein a polymeric binder content of greater than zero but less than 10% by weight of the fibers plus the weight of the coating is typically most preferred. This is not intended as limiting. For example, phenolic/PVB impregnated woven aramid fabrics are sometimes fabricated with a higher resin content of from about 20% to about 30%, although around 12% content is typically preferred.

Following weaving or consolidation of the fiber layers, an optional thermoplastic polymer layer may be attached to one or both of the outer surfaces of the fibrous composite via conventional methods. Suitable polymers for the thermoplastic polymer layer non-exclusively include thermoplastic polymers non-exclusively may be selected from the group consisting of polyolefins, polyamides, polyesters (particularly polyethylene terephthalate (PET) and PET copolymers), polyurethanes, vinyl polymers, ethylene vinyl alcohol copolymers, ethylene octane copolymers, acrylonitrile copolymers, acrylic polymers, vinyl polymers, polycarbonates, polystyrenes, fluoropolymers and the like, as well as co-polymers and mixtures thereof, including ethylene vinyl acetate (EVA) and ethylene acrylic acid. Also useful are natural and synthetic rubber polymers. Of these, polyolefin and polyamide layers are preferred. The preferred polyolefin is a polyethylene. Non-limiting examples of useful polyethylenes are low density polyethylene (LDPE), linear low density polyethylene (LLDPE), Medium Density Polyethylene (MDPE), linear medium density polyethylene (LMDPE), linear very-low density polyethylene (VLDPE), linear ultra-low density polyethylene (ULDPE), high density polyethylene (HDPE) and co-polymers and mixtures thereof. Also useful are SPUNFAB® polyamide webs commercially available from Spunfab, Ltd, of Cuyahoga Falls, Ohio (trademark registered to Keuchel Associates, Inc.), as well as THERMOPLAST™ and HELIOPLAST™ webs, nets and films, commercially available from Protechnic S.A. of Cernay, France. The thermoplastic polymer layer may be bonded to the composite surfaces using well known techniques, such as thermal lamination. Typically, laminating is done by positioning the individual layers on one another under conditions of sufficient heat and pressure to cause the layers to combine into a unitary film. The individual layers are positioned on one another, and the combination is then typically passed through the nip of a pair of heated laminating rollers by techniques well known in the art. Lamination heating may be conducted at temperatures ranging from about 95° C. to about 175° C., preferably from about 105° C. to about 175° C., at pressures ranging from about 5 psig (0.034 MPa) to about 100 psig (0.69 MPa), for from about 5 seconds to about 36 hours, preferably from about 30 seconds to about 24 hours.

The thickness of the individual fabrics/composites/fiber layers will correspond to the thickness of the individual fibers and the number of fiber layers incorporated into a fabric. A preferred woven fabric will have a preferred thickness of from about 25 μm to about 600 μm per layer, more preferably from about 50 μm to about 385 μm and most preferably from about 75 μm to about 255 μm per layer. A preferred non-woven fabric, i.e. a non-woven, single-layer, consolidated network, will have a preferred thickness of from about 12 μm to about 600 μm, more preferably from about 50 μm to about 385 μm and most preferably from about 75 μm to about 255 μm, wherein a single-layer, consolidated network typically includes two consolidated plies (i.e. two unitapes). Any thermoplastic polymer layers are preferably very thin, having preferred layer thicknesses of from about 1 μm to about 250 μm, more preferably from about 5 μm to about 25 μm and most preferably from about 5 μm to about 9 μm. Discontinuous webs such as SPUNFAB® non-woven webs are preferably applied with a basis weight of 6 grams per square meter (gsm). While such thicknesses are preferred, it is to be understood that other thicknesses may be produced to satisfy a particular need and yet fall within the scope of the present invention.

The fabrics/composites of the invention will have a preferred areal density prior to consolidation/molding of from about 20 grams/m² (0.004 lb/ft² (psf)) to about 1000 gsm (0.2 psf). More preferable areal densities for the fabrics/composites of this invention prior to consolidation/molding will range from about 30 gsm (0.006 psf) to about 500 gsm (0.1 psf). The most preferred areal density for fabrics/composites of this invention will range from about 50 gsm (0.01 psf) to about 250 gsm (0.05 psf) prior to consolidation/molding. Articles of the invention comprising multiple fiber layers stacked one upon another and consolidated will have a preferred composite areal density of from about 1000 gsm (0.2 psf) to about 40,000 gsm (8.0 psf), more preferably from about 2000 gsm (0.40 psf) to about 30,000 gsm (6.0 psf), more preferably from about 3000 gsm (0.60 psf) to about 20,000 gsm (4.0 psf), and most preferably from about 3750 gsm (0.75 psf) to about 15,000 gsm (3.0 psf). A typical range for composite articles shaped into helmets is from about 7,500 gsm (1.50 psf) to about 12,500 gsm (2.50 psf).

The fabrics of the invention may be used in various applications to form a variety of different ballistic resistant articles using well known techniques, including flexible, soft armor articles as well as rigid, hard armor articles. For example, suitable techniques for forming ballistic resistant articles are described in, for example, U.S. Pat. Nos. 4,623,574, 4,650,710, 4,748,064, 5,552,208, 5,587,230, 6,642,159, 6,841,492 and 6,846,758, all of which are incorporated herein by reference to the extent not incompatible herewith. The composites are particularly useful for the formation of hard armor and shaped or unshaped sub-assembly intermediates formed in the process of fabricating hard armor articles.

By "hard" armor is meant an article, such as helmets, panels for military vehicles, or protective shields, which have sufficient mechanical strength so that it maintains structural rigidity when subjected to a significant amount of stress and is capable of being freestanding without collapsing. Such hard articles are preferably, but not exclusively, formed using a high tensile modulus binder material.

The structures can be cut into a plurality of discrete sheets and stacked for formation into an article or they can be formed into a precursor which is subsequently used to form an article. Such techniques are well known in the art. In a most preferred embodiment of the invention, a plurality of fiber layers are provided, each comprising a consolidated plurality of fiber plies, wherein a thermoplastic polymer is bonded to at least one outer surface of each fiber layer either before, during or after a consolidation step which consolidates the plurality of fiber plies, wherein the plurality of fiber layers are subsequently merged by another consolidation step which consolidates the plurality of fiber layers into an armor article or sub-assembly of an armor article.

The ballistic resistance properties of the fibrous composites of the invention, including both ballistic penetration resistance and backface signature, may be measured according to well known techniques in the art.

The following examples serve to illustrate the invention.

EXAMPLES

The impact of fiber finish removal and optionally other fiber surface treatments on the dynamic storage modulus and backface signature performance of various composites was assessed, generating results as identified in Table 2 below. The fiber processing techniques were conducted as follows:

Fiber Finish Removal

A plurality of multi-filament fibers was unwound from a plurality of fiber spools (one spool per multi-filament fiber) and then passed through a fixed collimating comb to organize the fibers into an evenly spaced fiber web. The fiber web was then directed through a pre-soak water bath containing de-ionized water, with an approximate residence time of about 18 seconds. After exiting the pre-soak water bath, the fibers were rinsed by a bank of 30 water nozzles. Water pressure of each water nozzle was approximately 42 psi with a water flow rate of approximately 0.5 gallons per minute per nozzle. The water exiting the nozzles was formed as a relatively flat stream and the angle of water contact on the fibers was either 0° or 30° relative to the angle of incidence of the stream emitting from adjacent nozzles. Water temperature was measured as 28.9° C. Line speeds through the pre-soak water bath and through the bank of water nozzles ranged from about 4 m/min to about 20 m/min. The water in the soak bath and water delivered to the nozzles was deionized by first passing through a separate de-ionizing system. The washed fibers were then dried and transferred for further processing.

Table 1 summarizes representative examples provided solely to illustrate how certain washing variables affect the quantity of finish removed from the fiber. Each sample consisted of 4 ends bundled together on one sample spool. Each sample was run for at least 400 ft which totaled 60 g of fiber per sample. The % residue on the fiber represents a gravimetrically determined measurement of the amount of finish remaining on the fiber after washing per the specified conditions in the Table. The gravimetric measurement is based on a comparison with the amount of finish present on unwashed control fibers.

TABLE 1

| Sample | Nozzle Style | Nozzle Pressure (psi) | Line Speed (Ft/min) | Nozzle Output (gpm) | % Residue on Fiber |
|---|---|---|---|---|---|
| I | A1 | 42 | 15 | 0.20 | 2.3 |
| II | B1 | 30 | 15 | 0.29 | 2.4 |
| III | C1 | 30 | 15 | 0.41 | 3.1 |
| IV | C2 | 15 | 15 | 0.30 | 3.1 |
| V | A2 | 42 | 15 | 0.20 | 4.0 |
| VI | B2 | 30 | 15 | 0.29 | 4.1 |
| VII | A3 | 56 | 50 | 0.23 | 5.0 |
| VIII | C3 | 15 | 15 | 0.30 | 5.1 |
| IX | A4 | 56 | 30 | 0.23 | 5.5 |
| X | C4 | 30 | 15 | 0.41 | 5.9 |
| XI | C5 | 34 | 30 | 0.44 | 5.9 |
| XII | C6 | 34 | 60 | 0.44 | 6.2 |

Corona Treatment

An 18-inch wide web of washed fibers was continuously passed through a corona treater having 30-inch wide electrodes at a rate of approximately 15 ft/min, with the corona treater set to a power of 2 kW. This resulted in a power distribution over the area of the fibers, measured in watt density, of 2000 W/(2.5 Ft×15-FPM) or 53 Watts/ft$^2$/min applied to the fibers. The residence time of the fibers within the corona field was approximately 2 seconds. Treatment was conducted under standard atmospheric pressure.

Plasma Treatment

A 29-inch wide web of washed fibers was continuously passed through an atmospheric plasma treater (model: Enercon Plasma3 Station Model APT12DF-150/2, from Enercon Industries Corp., having 29-inch wide electrodes) at a rate of approximately 12 ft/min, with the plasma treater set to a power of 2 kW. This resulted in a power distribution over the area of the fibers, measured in watt density, of 2000 W/(29 in.×12-FPM) or 67 Watts/ft$^2$/min applied to the fibers. The residence time of the fibers within the plasma treater was approximately 2 seconds. Treatment was conducted under standard atmospheric pressure.

Measurement of Dynamic Storage Modulus

In all of the inventive examples illustrated below, dynamic mechanical analysis was performed on non-woven fiber layers to measure the dynamic storage modulus. Testing was conducted using an RSA 3 DMA testing machine from TA Instruments.

The fibers of the tested composites were embedded in various polymeric binder (polymeric matrix) materials. Each composite comprised the same polyethylene fiber type with each comprising a different anionic, aliphatic polyester-based polyurethane coating on the fibers. Various treatments are compared to show the effect of the fiber treatments where the fiber treatments are the only variables. The composites were formed by molding two 2-ply fiber layers together at a temperature of about 270° F. (132° C.) and at a pressure of about 2777 psi to form a 4-ply composite.

The testing procedure was as follows:
1. Two 12" by 12" cross-plied, 2-ply unidirectional fiber layers were molded in a press at 270° F. and 2777 psi to produce a 4-ply panel.
2. A specimen approximately 6-8 mm wide is cut from the panel on the basis (45 degrees to the machine and cross directions).
3. The width and thickness of the specimen were measured.
4. The gap distance between the upper and lower clamps of the TA Instruments RSA 3 DMA apparatus was set at 20 mm.
5. The test frequency was set at 10 rad/s and applied strain at 0.1%.
6. The sample was heated starting at approximately 25° C. and the dynamic storage modulus (E') was measured at intervals of 1° C. up to 130° C.
7. The dynamic storage modulus was recorded as a function of temperature, including recording values at 25° C. and 71° C. (160° F.).
8. Two specimens from each sample were tested according to this method and the results were averaged.

$V_{50}$ Measurement $V_{50}$ data was acquired taken under conventionally known standardized techniques, particularly per the conditions of Department of Defense Test Method Standard MIL-STD-662F.

Backface Signature Measurement

The backface signature data identified in Table 3A was measured by a method of new design similar to the method of NIJ Standard 0101.04, Type IIIA, but rather than laying the composite article directly on a flat clay block the composite was spaced apart from the clay block by ½ inch (12.7 mm) by inserting a custom machined spacer element between the composite article and the clay block. The custom machined spacer element comprised an element having a border and an interior cavity defined by said border wherein the clay was exposed through the cavity, and wherein the spacer was positioned in direct contact with front surface of the clay. Projectiles were fired at the composite articles at target locations corresponding to the interior cavity of the spacer. The projectiles impacted the composite article at locations corresponding to the interior cavity of the spacer, and each projectile impact caused a measurable depression in the clay. All of the BFS measurements in Table 3A refer only to the depth of the depression in the clay as per this method and do not take into account the depth of the spacer element, i.e. the BFS measurements in Table 3A do not include the actual distance between the composite and the clay.

Delamination Measurement

Delamination in Table 3A refers to the measurement of the depth of rear deformation of the actual tested panels, rather than the depth of depression in the backing material. Such is referred to as "delamination" because it is not the clay depression which is being measured. This measurement of delamination will be less than the BFS measurement plus the ½" (12.7 mm) air gap depth because after a projectile impact, the fabric at the area of impact partially retracts. The delamination measurement is taken after said retraction, while the BFS measurement with the air gap method described herein records the full extent of rear deformation of the fabric. Deformation after said retraction is typically measured by cutting a cross-section of the panel and measuring the depth from the plane of the undamaged rear surface of the panel to the deepest outer portion of the deformed area.

For each example, BFS was measured for 12"×12" square samples having an areal density of 2.0 lb/ft$^2$ (psf) and a fiber areal density (areal density of a single ply of parallel fibers, i.e. one unitape) of 53 grams/m$^2$ (gsm). For each example, BFS was measured against a 9 mm, 124-grain FMJ RN projectile fired at a velocity of about 1430 feet/second (fps)±30 fps.

Table 2 illustrates the differences in measured dynamic storage modulus when comparing fabrics formed from unwashed and untreated fibers relative to fabrics formed from fibers that were subjected to various treatments. Each of products A, B and C each comprised the same polyethylene fiber type and each comprised a different anionic, aliphatic polyester-based polyurethane coating on the fibers.

TABLE 2

| Treatment | PROD A Dynamic Storage Modulus (dyn/cm$^2$) ×10$^9$ Ambient | PROD A Dynamic Storage Modulus (dyn/cm$^2$) ×10$^9$ 160° F. | PROD B Dynamic Storage Modulus (dyn/cm$^2$) ×10$^9$ Ambient | PROD B Dynamic Storage Modulus (dyn/cm$^2$) ×10$^9$ 160° F. | PROD C Dynamic Storage Modulus (dyn/cm$^2$) ×10$^9$ Ambient | PROD C Dynamic Storage Modulus (dyn/cm$^2$) ×10$^9$ 160° F. |
|---|---|---|---|---|---|---|
| None | 12.0 | 5.7 | 7.1 | 4.0 | 6.5 | 3.5 |
| Washed | 9.6 | 6.5 | 9.2 | 5.3 | 9.3 | 4.4 |
| Corona | 15.0 | 7.1 | 7.7 | 3.8 | 13.0 | 5.2 |
| Plasma (Ar/O$_2$ 90/10) | 19.0 | 7.6 | 7.4 | 3.2 | 8.0 | 3.1 |
| Plasma (He/O$_2$ 90/10) | 28.0 | 11.0 | 10.0 | 4.6 | 9.8 | 4.3 |
| Washed & Plasma (Ar/O$_2$ 90/10) | 26.0 | 13.0 | 9.7 | 4.2 | 12.0 | 5.5 |

Table 3A illustrates the differences in measured BFS and delamination when comparing fabrics formed from unwashed and untreated fibers relative to fabrics formed from fibers that were subjected to various treatments. Each of products I-VI comprised the same polyethylene fiber type and each comprised a different anionic, aliphatic polyester-based polyurethane coating on the fibers. The last two columns in Table 3A identifying BFS plus ½" (12.7 mm) gap minus delamination identify the amount of fabric retraction and illustrate the greater accuracy of the air gap spacer BFS measurement method for measuring the full expected extent of BFS of hard armor in actual field use.

TABLE 3A

| Example | Product | Fiber Treatment | BFS @ 2.0 psf RT (mm) | BFS @ 2.0 psf 160° F. (71.11° C.) (mm) | Delamination @ 2.0 psf RT (mm) | Delamination @ 2.0 psf 160° F. (71.11° C.) (mm) | BFS plus ½" gap minus Delam @ RT (mm) | BFS plus ½" gap minus Delam @ 160° F. (mm) |
|---|---|---|---|---|---|---|---|---|
| 1 | I | None | 9.4 | 13.1 | 17.3 | 14.7 | 4.8 | 11.1 |
| 2 | I | Plasma Only Ar/O2 90/10 (2 kW) | 6.5 | 9.8 | 13.1 | 12.3 | 6.1 | 10.2 |

TABLE 3A-continued

| Example | Product | Fiber Treatment | BFS @ 2.0 psf RT (mm) | BFS @ 2.0 psf 160° F. (71.11° C.) (mm) | Delamination @ 2.0 psf RT (mm) | Delamination @ 2.0 psf 160° F. (71.11° C.) (mm) | BFS plus ½" gap minus Delam @ RT (mm) | BFS plus ½" gap minus Delam @ 160° F. (mm) |
|---|---|---|---|---|---|---|---|---|
| 3 | I | Wash & Plasma Ar/O2 90/10 (3 kW) | 3.4 | 6.3 | 11.0 | 11.5 | 5.1 | 7.5 |
| 4 | II | None | 8.3 | 11.3 | 16.3 | 17.0 | 4.7 | 7.0 |
| 5 | II | Washed | 10.5 | 11.5 | 14.5 | 18.4 | 8.7 | 5.8 |
| 6 | II | Plasma Only Ar/O2 90/10 (2 kW) | 5.3 | 7.5 | 13.3 | 14.1 | 4.7 | 6.1 |
| 7 | II | Wash & Plasma Ar/O2 90/10 (3 kW) | 1.9 | 4.7 | 12.3 | 11.9 | 2.3 | 5.5 |
| 8 | II | Wash & Plasma Ar/O2 90/10 (1.5 kW) | 2.3 | 4.1 | 12.1 | 15.5 | 2.8 | 1.3 |
| 9 | III | None | 12.4 | 14.9 | 15.6 | 14.9 | 9.5 | 12.7 |
| 10 | III | Washed | 11.5 | 10.3 | 11.8 | 14.3 | 12.4 | 8.7 |
| 11 | III | Plasma Only Ar/O2 90/10 (2 kW) | 6.9 | 11.7 | 9.8 | 10.1 | 9.8 | 14.3 |
| 12 | III | Wash & Plasma Ar/O2 90/10 (3 kW) | 5.1 | 6.1 | 12.8 | 12.1 | 5.1 | 6.7 |
| 13 | IV | None | 5.3 | 14.3 | 12.5 | 14.8 | 5.5 | 12.2 |
| 14 | IV | Wash & Plasma Ar/O2 90/10 (3 kW) | 6.3 | 9.6 | 14.3 | 13.8 | 4.7 | 8.6 |
| 15 | V | Wash & Plasma Ar/O2 90/10 (3 kW) | 3.8 | 6.1 | 14.9 | 13.7 | 1.6 | 5.1 |
| 16 | VI | Wash & Plasma Ar/O2 90/10 (3 kW) | 3.1 | 6.4 | 12.8 | 13.6 | 3.1 | 5.5 |

Table 3B illustrates differences in ballistic penetration resistance ($V_{50}$) and dynamic storage modulus (E') properties as distinguished by fiber treatment.

TABLE 3B

| Example | Product | Fiber Treatment | $V_{50}$ 17 gr. @ 1.0 psf (fps) | Dynamic storage modulus E' (dyn/cm$^2$) 77° F. | Dynamic storage modulus E' (dyn/cm$^2$) 160° F. |
|---|---|---|---|---|---|
| 1 | I | None | 1848 | 6.5 | 3.5 |
| 2 | I | Plasma Only Ar/O2 90/10 (2 kW) | 1810 | 8.0 | 3.1 |
| 3 | I | Wash & Plasma Ar/O2 90/10 (3 kW) | 1894 | 12.0 | 5.5 |
| 4 | II | None | 1798 | 12.0 | 5.7 |
| 5 | II | Washed | 1899 | 9.6 | 6.5 |
| 6 | II | Plasma Only Ar/O2 90/10 (2 kW) | 1771 | 19.0 | 7.6 |
| 7 | II | Wash & Plasma Ar/O2 90/10 (3 kW) | 1752 | 26.0 | 13.0 |
| 8 | II | Wash & Plasma Ar/O2 90/10 (1.5 kW) | 1767 | — | — |
| 9 | III | None | 1902 | 7.1 | 4.0 |
| 10 | III | Washed | 1889 | 9.2 | 5.3 |
| 11 | III | Plasma Only Ar/O2 90/10 (2 kW) | 1828 | 7.4 | 3.2 |
| 12 | III | Wash & Plasma Ar/O2 90/10 (3 kW) | 1897 | 9.7 | 4.2 |
| 13 | IV | None | 1813 | — | — |
| 14 | IV | Wash & Plasma Ar/O2 90/10 (3 kW) | 1814 | — | — |
| 15 | V | Wash & Plasma Ar/O2 90/10 (3 kW) | 1917 | — | — |
| 16 | VI | Wash & Plasma Ar/O2 90/10 (3 kW) | 1850 | — | — |

While the present invention has been particularly shown and described with reference to preferred embodiments, it will be readily appreciated by those of ordinary skill in the art that various changes and modifications may be made without departing from the spirit and scope of the invention. It is intended that the claims be interpreted to cover the disclosed embodiment, those alternatives which have been discussed above and all equivalents thereto.

What is claimed is:

1. A fibrous composite comprising a plurality of adjoined fiber layers, each fiber layer comprising fibers having surfaces that are at least partially covered with a polymeric material, wherein said fibers are predominantly free of a fiber surface finish such that said polymeric material is predominantly in direct contact with the fiber surfaces; said fibrous composite having a dynamic storage modulus that is greater than the dynamic storage modulus of a comparable fibrous composite having fiber surfaces that are predominantly covered with a fiber surface finish wherein such a fiber surface finish is between the fiber surfaces and the polymeric material.

2. The fibrous composite of claim 1, wherein the composite has a dynamic storage modulus of at least $8.0 \times 10^9$ dyn/cm$^2$ as measured at 25° C. (77° F.).

3. The fibrous composite of claim 2 which composite has a $V_{50}$ value of at least about 1750 feet/sec (fps) (533.40 m/s) against a 9 mm projectile in accordance with Department of Defense Test Method Standard MIL-STD-662F.

4. The fibrous composite of claim 2 wherein said composite has a backface signature of less than about 8 mm when impacted with a 124-grain, 9 mm FMJ RN projectile fired at a velocity of from about 427 m/s to about 445 m/s (1430 feet/second (fps) ±30 fps), wherein backface signature is measured for a composite having an areal density of 2.0 psf.

5. The fibrous composite of claim 1, wherein the composite has a dynamic storage modulus of at least about $12.0 \times 10^9$ $dyn/cm^2$ as measured at 25° C. (77° F.).

6. The fibrous composite of claim 1, wherein the composite has a dynamic storage modulus of at least about $20.0 \times 10^9$ $dyn/cm^2$ as measured at 25° C. (77° F.).

7. The fibrous composite of claim 1 wherein said composite comprises polyethylene fibers.

8. The fibrous composite of claim 1 wherein said composite comprises a consolidated plurality of cross-plied, non-woven, unidirectional fiber plies, wherein said polymeric material comprises at least one thermoplastic polymeric binder, and wherein each fiber layer of the composite is impregnated with said thermoplastic polymeric binder.

9. The fibrous composite of claim 1 wherein the fiber surfaces are substantially free of a fiber surface finish between the fiber surface and the polymeric material such that said polymeric material is substantially in direct contact with the fiber surfaces, and wherein patches of residual finish are present on the fiber surfaces between the fiber surface and the polymeric material, wherein at least 75% of the fiber surface area is not covered by the residual fiber surface finish.

10. The fibrous composite of claim 1 wherein said composite has a composite areal density of from about 3,750 $g/m^2$ (0.75 psf) to about 12,500 $g/m^2$ (2.50 psf).

11. The fibrous composite of claim 1 wherein said composite comprises fibers having a tenacity of 20 g/denier or more.

* * * * *